(12) United States Patent
Manwaring et al.

(10) Patent No.: US 8,915,909 B2
(45) Date of Patent: Dec. 23, 2014

(54) IMPEDANCE MATCHING CIRCUIT

(75) Inventors: Preston Manwaring, Farmington, UT (US); Kim Manwaring, Phoenix, AZ (US); Mark Stringham, Salt Lake City, UT (US); Phil Eggers, Cottonwood Heights, UT (US)

(73) Assignee: Domain Surgical, Inc., Salt Lake City, UT (US)

( * ) Notice: Subject to any disclaimer, the term of this patent is extended or adjusted under 35 U.S.C. 154(b) by 400 days.

(21) Appl. No.: 13/441,860

(22) Filed: Apr. 7, 2012

(65) Prior Publication Data
US 2012/0259323 A1 Oct. 11, 2012

Related U.S. Application Data

(60) Provisional application No. 61/473,722, filed on Apr. 8, 2011.

(51) Int. Cl.
| | |
|---|---|
| *A61B 18/04* | (2006.01) |
| *A61B 18/12* | (2006.01) |
| *A61B 18/08* | (2006.01) |
| *A61B 18/14* | (2006.01) |
| *A61B 18/00* | (2006.01) |

(52) U.S. Cl.
CPC .......... *A61B 18/1206* (2013.01); *A61B 18/085* (2013.01); *A61B 18/1477* (2013.01); *A61B 2018/00107* (2013.01); *A61B 2018/00577* (2013.01); *A61B 2018/00994* (2013.01); *A61B 2018/141* (2013.01)
USPC .......................................................... 606/27

(58) Field of Classification Search
CPC ............. A61B 18/085; A61B 18/1206; A61B 18/1477; A61B 2018/00107; A61B 2018/00577; A61B 2018/00994; A61B 2018/141

USPC .......................................................... 606/27
See application file for complete search history.

(56) References Cited

U.S. PATENT DOCUMENTS

| | | |
|---|---|---|
| 300,155 A | 6/1884 | Starr |
| 770,368 A | 9/1904 | Heath |
| 1,104,053 A | 7/1914 | Lea |
| 1,280,052 A | 9/1918 | Lidberg |

(Continued)

FOREIGN PATENT DOCUMENTS

| | | |
|---|---|---|
| EP | 0033958 | 8/1981 |
| EP | 0 130 671 | 9/1985 |

(Continued)

OTHER PUBLICATIONS

International Preliminary Report on Patentability from related PCT Patent Application No. PCT/US2012/032659, Nov. 23, 2012.

(Continued)

*Primary Examiner* — George Manuel
(74) *Attorney, Agent, or Firm* — Bateman IP

(57) ABSTRACT

An impedance matching circuit may be used to adjust for manufacturing and design tolerances in a surgical instrument. The matching circuit may match the load of a thermal element with the impedance of a power source used to deliver electrical energy to the surgical instrument. The matching circuit may include capacitors, inductors, coaxial cables, varactors, transformers, resistors, and/or combinations thereof. The matching circuit may also comprise a circuit board or flex board layers which may be modified to adjust the impedance of the load.

21 Claims, 52 Drawing Sheets

(56) References Cited

U.S. PATENT DOCUMENTS

| | | |
|---|---|---|
| 1,335,987 A | 4/1920 | Reid |
| 1,366,231 A | 1/1921 | Winter et al. |
| 1,401,104 A | 12/1921 | Kruesheld |
| 1,794,296 A | 2/1931 | Hyams |
| 2,027,854 A | 1/1936 | Breth et al. |
| 2,050,904 A | 8/1936 | Trice |
| 2,120,598 A | 6/1938 | Beuoy |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 12/1954 | Stone |
| 2,735,797 A | 2/1956 | Schjeldahl |
| 2,782,290 A | 2/1957 | Lannan et al. |
| 2,831,242 A | 4/1958 | Kieffer et al. |
| 2,846,560 A | 8/1958 | Jacoby et al. |
| 2,863,036 A | 12/1958 | Mitchell et al. |
| 2,947,345 A | 8/1960 | Schjeldahl |
| 2,960,592 A | 11/1960 | Pierce |
| 3,084,242 A | 4/1963 | Vogler et al. |
| 3,213,259 A | 10/1965 | Bennet et al. |
| 3,350,544 A | 10/1967 | Lennox |
| 3,352,011 A | 11/1967 | Alexander et al. |
| 3,400,252 A | 9/1968 | Hayakawa |
| 3,404,202 A | 10/1968 | Carlson et al. |
| 3,413,442 A | 11/1968 | Buiting et al. |
| 3,414,705 A | 12/1968 | Marcoux |
| 3,434,476 A | 3/1969 | Shaw et al. |
| 3,501,619 A | 3/1970 | Buiting et al. |
| 3,515,837 A | 6/1970 | Ando |
| 3,520,043 A | 7/1970 | Darling |
| 3,556,953 A | 1/1971 | Schulz |
| 3,768,482 A | 10/1973 | Shaw |
| 3,825,004 A | 7/1974 | Durden, III |
| 3,826,263 A | 7/1974 | Cage et al. |
| 3,834,392 A | 9/1974 | Lampman et al. |
| 3,978,312 A | 8/1976 | Barton et al. |
| RE29,088 E | 12/1976 | Shaw |
| 4,089,336 A | 5/1978 | Cage et al. |
| 4,091,813 A | 5/1978 | Shaw et al. |
| RE30,190 E | 1/1980 | Shaw |
| 4,185,632 A | 1/1980 | Shaw |
| 4,196,734 A | 4/1980 | Harris |
| 4,198,957 A | 4/1980 | Cage et al. |
| 4,206,759 A | 6/1980 | Shaw |
| 4,207,896 A | 6/1980 | Shaw |
| 4,209,017 A | 6/1980 | Shaw |
| 4,256,945 A | 3/1981 | Carter et al. |
| 4,359,052 A | 11/1982 | Staub |
| 4,364,390 A | 12/1982 | Shaw |
| 4,371,861 A | 2/1983 | Abdelrahman et al. |
| 4,374,517 A | 2/1983 | Hagiwara |
| RE31,723 E | 11/1984 | Shaw |
| 4,481,057 A | 11/1984 | Beard |
| 4,485,810 A | 12/1984 | Beard |
| 4,492,231 A | 1/1985 | Auth |
| 4,493,320 A | 1/1985 | Treat |
| 4,523,084 A | 6/1985 | Tamura et al. |
| 4,549,073 A | 10/1985 | Tamura et al. |
| 4,600,018 A | 7/1986 | James et al. |
| 4,622,966 A | 11/1986 | Beard |
| 4,701,587 A | 10/1987 | Carter et al. |
| 4,752,673 A | 6/1988 | Krumme |
| 4,807,620 A | 2/1989 | Strul |
| 4,839,501 A | 6/1989 | Cowell |
| 4,848,337 A | 7/1989 | Shaw et al. |
| 4,877,944 A | 10/1989 | Cowell et al. |
| 4,914,267 A | 4/1990 | Derbyshire |
| 4,915,100 A | 4/1990 | Green |
| 4,927,413 A | 5/1990 | Hess |
| 4,938,761 A | 7/1990 | Ensslin |
| 5,003,991 A | 4/1991 | Takayama et al. |
| 5,047,025 A | 9/1991 | Taylor et al. |
| 5,053,595 A | 10/1991 | Derbyshire |
| 5,057,106 A | 10/1991 | Kasevich et al. |
| 5,071,419 A | 12/1991 | Rydell et al. |
| 5,087,256 A | 2/1992 | Taylor et al. |
| 5,087,804 A | 2/1992 | McGaffigan |
| 5,098,429 A | 3/1992 | Sterzer |
| 5,107,095 A | 4/1992 | Derbyshire |
| 5,182,427 A | 1/1993 | McGaffigan |
| 5,189,271 A | 2/1993 | Derbyshire |
| 5,197,649 A | 3/1993 | Bessler et al. |
| 5,203,782 A | 4/1993 | Gudov et al. |
| 5,211,646 A | 5/1993 | Alperovich et al. |
| 5,217,460 A | 6/1993 | Knoepfler |
| 5,300,068 A | 4/1994 | Rosar et al. |
| 5,300,750 A | 4/1994 | Carter, Jr. et al. |
| 5,308,311 A | 5/1994 | Eggers et al. |
| 5,318,564 A | 6/1994 | Eggers |
| 5,370,675 A | 12/1994 | Edwards et al. |
| 5,376,094 A | 12/1994 | Kline |
| 5,382,247 A | 1/1995 | Cimino et al. |
| 5,400,267 A | 3/1995 | Denen et al. |
| 5,411,508 A | 5/1995 | Bessler et al. |
| 5,423,808 A | 6/1995 | Edwards et al. |
| 5,425,731 A | 6/1995 | Daniel et al. |
| 5,445,635 A | 8/1995 | Denen et al. |
| 5,472,443 A | 12/1995 | Cordis et al. |
| 5,475,203 A | 12/1995 | McGaffigan |
| 5,480,397 A | 1/1996 | Eggers |
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |
| 5,571,153 A | 11/1996 | Wallsten |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,402 A | 1/1998 | Heim |
| 5,807,392 A | 9/1998 | Eggers |
| 5,827,269 A | 10/1998 | Saadat |
| 5,836,874 A | 11/1998 | Swanson et al. |
| 5,836,943 A | 11/1998 | Miller, III |
| 5,911,719 A | 6/1999 | Eggers |
| 5,964,759 A | 10/1999 | Yamanashi et al. |
| 6,004,316 A | 12/1999 | Laufer |
| 6,006,755 A | 12/1999 | Edwards |
| 6,015,415 A | 1/2000 | Avellanet |
| 6,035,238 A | 3/2000 | Ingle et al. |
| 6,038,017 A | 3/2000 | Pinsukanjana et al. |
| 6,066,138 A | 5/2000 | Sheffer et al. |
| 6,161,048 A | 12/2000 | Sluijter et al. |
| 6,190,382 B1 | 2/2001 | Ormsby et al. |
| 6,228,084 B1 | 5/2001 | Kirwan, Jr. |
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 | 2/2002 | Ashley |
| 6,358,273 B1 | 3/2002 | Strul et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,726,683 B1 | 4/2004 | Shaw |
| 6,821,273 B2 | 11/2004 | Mollenauer |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,011,656 B2 | 3/2006 | McGaffigan |
| 7,083,613 B2 | 8/2006 | Treat |
| 7,122,030 B2 | 10/2006 | Flores et al. |

(56) References Cited

U.S. PATENT DOCUMENTS

| | | |
|---|---|---|
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,473,250 B2 | 1/2009 | Makin et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,702,397 B2 | 4/2010 | Fredricks et al. |
| 7,871,406 B2 | 1/2011 | Nields et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 8,100,896 B2 | 1/2012 | Rodhajsky |
| 2001/0014804 A1 | 8/2001 | Goble et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0068931 A1 | 6/2002 | Wong et al. |
| 2002/0120261 A1 | 8/2002 | Balbierz et al. |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0144660 A1 | 7/2003 | Mollenauer |
| 2003/0171747 A1 | 9/2003 | Kanehira et al. |
| 2003/0199755 A1 | 10/2003 | Halperin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0127706 A1 | 6/2006 | Goebel et al. |
| 2006/0142824 A1* | 6/2006 | Zikorus et al. .................. 607/96 |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0106294 A1 | 5/2007 | Nesbitt |
| 2007/0127897 A1 | 6/2007 | John et al. |
| 2007/0131428 A1 | 6/2007 | Boestert |
| 2007/0173811 A1 | 7/2007 | Couture et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0228244 A1 | 9/2010 | Hancock et al. |
| 2010/0268218 A1 | 10/2010 | Ormsby et al. |

(56) References Cited

U.S. PATENT DOCUMENTS

| | | | |
|---|---|---|---|
| 2011/0004204 | A1 | 1/2011 | Dodde et al. |
| 2011/0054456 | A1 | 3/2011 | Thompson et al. |
| 2011/0152857 | A1 | 6/2011 | Ingle |

FOREIGN PATENT DOCUMENTS

| | | |
|---|---|---|
| EP | 2070486 | 6/2009 |
| GB | 2 022 974 | 12/1978 |
| GB | 1 546 624 | 5/1979 |
| JP | 03-051179 | 6/1987 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |
| WO | WO-2004/076146 | 9/2004 |
| WO | WO-2006/017517 | 2/2006 |
| WO | WO-2006/029649 | 3/2006 |
| WO | WO 2007080578 A2 | 7/2007 |
| WO | WO-2008/060668 | 5/2008 |

OTHER PUBLICATIONS

International Preliminary Report on Patentability from related PCT Patent Application No. PCT/US2012/038005, Nov. 23, 2012.

International Preliminary Report on Patentability from related PCT Patent Application No. PCT/US2012/032656, Oct. 23, 2012.

Translation of Office Action from related Japanese Patent Application No. 2012-506188, PCT US2010-031114.

Written Opinion of the International Preliminary Examining Authority from related PCT Patent Application No. PCT/US2011/050417, Feb. 6, 2013.

Visioli, Antonio. Practice PID Control: London: Springer-Verlag, 2006. 1-18. Print.

Center for Research in Scientific Computation. *A Domain Wall Theory for Ferroelectric Hysteresis*, Jan. 1999.

International Preliminary Report on Patentability from related PCT Patent Application No. PCT/US2010/031114, Nov. 1, 2011.

International Search Report from related PCT Patent Application No. PCT/U52010/031114, Jan. 21, 2011.

Metcal Soldering Iron Catalog—2006.

URSI EMTS 2004, pp. 489-491, *Electromagnetic Probes for Living Tissue Cauterization*.

International Search Report and Written Opinion from related PCT Application US2012/032661, Aug. 19, 2013.

International Search Report and Written Opinion from related PCT Application US2012/038005, Nov. 19, 2013.

"High Temp Metals." NI2001201 Technical Data. High Temp Metals, Inc., n.d. Web. Jul. 13, 2012. <http://www.hightempmetals.com/techdatafnitempNi200data.php.

International Search Report and Written Opinion from related PCT Application US2012/032659, Oct. 8, 2013.

International Search Report and Written Opinion from related PCT Application US2012/032565, Oct. 8, 2013.

International Preliminary Report on Patentability from related PCT Patent Application No. PCT/US2011/050417, Apr. 12, 2012.

International Preliminary Report on Patentability from related PCT Patent Application No. PCT/US2012/055229, Feb. 1, 2013.

International Preliminary Report on Patentability from related PCT Patent Application No. PCT/US2012/068027, Feb. 25, 2013.

\* cited by examiner

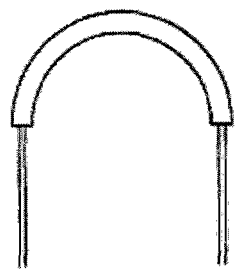 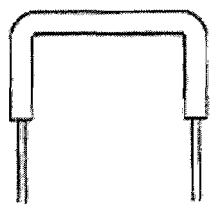 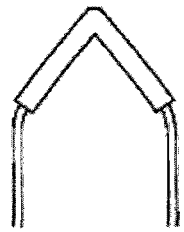
FIG. 16A    FIG. 16B    FIG. 16C
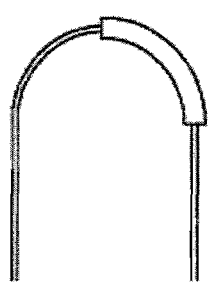 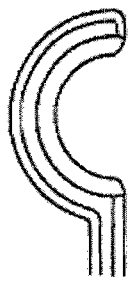 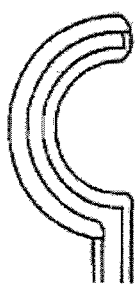 
FIG. 16D    FIG. 16E    FIG. 16F    FIG. 16G

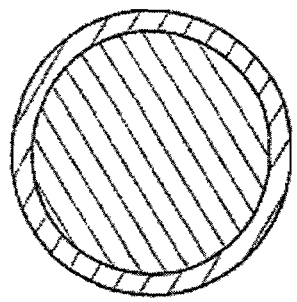
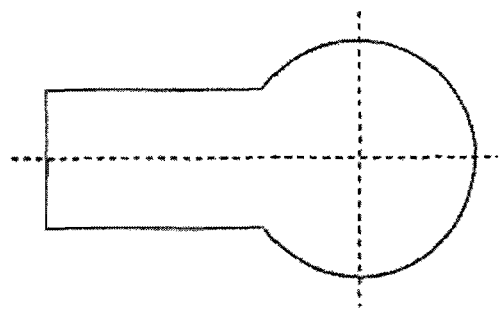
FIG. 22  FIG. 23A
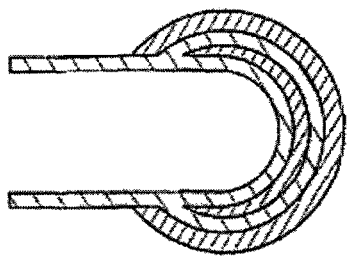
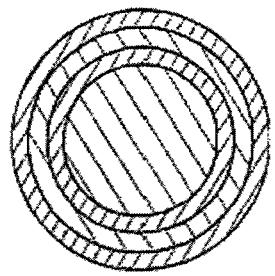
FIG. 23B  FIG. 24

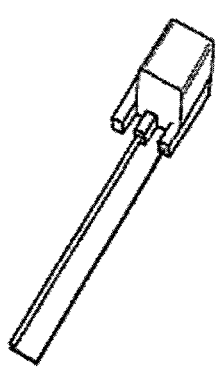 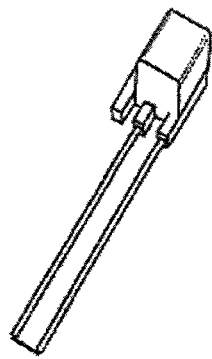 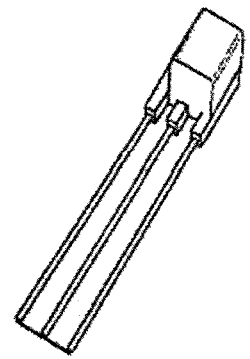
FIG. 27A  FIG. 27B  FIG. 27C
FIG. 27D

IMPEDANCE MATCHING CIRCUIT

PRIORITY

The present application claims the benefit of U.S. Provisional Patent Application Ser. No. 61/473,722, filed Apr. 8, 2011, which is incorporated herein by reference in its entirety.

THE FIELD OF THE INVENTION

The present invention relates to power transfer. More specifically, the present invention relates to optimum power transfer from a power source to a thermal surgical instrument.

BACKGROUND

Circuits may be designed with maximum voltage to load, maximum power to load or, sometimes, no thought to power or voltage transfer. In many situations, maximum power transfer is desirable, as it provides maximum power to the load. It is believed that maximum power transfer may be achieved by matching the impedance of the source to the load (and any intermediate lines or components). Circuits may use a matching network on the source side and load side (see FIG. 1A) or on one side only.

In general, impedance has a complex value; this means that loads (symbolized as Z) generally have a resistance component (symbolized as R) which forms the real part of Z and a reactance component (symbolized as X) which forms the imaginary part of Z. Power transfer theory dictates that for maximum power to be transferred, the source impedance ($Z_S$) should equal the complex conjugate of the load impedance ($Z_L$) such that the following equation holds true: $R_S+jX_S=R_L-jX_L$ (see FIG. 1B). As reactance X is variable with frequency, the matching network is generally tuned to one frequency.

Matching the load to the characteristic impedance ($Z_0$) of the transmission line allows reflectionless matching, minimizing reflections from the load. Thus, a transmission line connecting the source and load together would ideally be the same impedance: $Z_L=Z_0=Z_S$.

While in an ideal world, $Z_1$, $Z_0$ and $Z_L$ would be immutable and the same for every product produced, the impedances may be variable due to tolerances and design in manufacturing. Therefore, there is a need to customize each circuit to match impedances in a cost efficient manner.

SUMMARY OF THE INVENTION

It is an object of the present invention to provide an improved impedance matching circuit for a thermal surgical instrument.

According to one aspect of the invention, a conductive layer may be used as a variable capacitor. The conductive layer may be formed as part of a circuit board, flex board, etc. As the system monitors standing wave ratio, portions of the circuit board may be removed until a minimum of the standing wave ratio is obtained. Two conductive layers may be used to provide adjustments for the series capacitance and parallel capacitance. Removing part of a conductive layer from one side of the circuit board may adjust the series capacitance, while removing part of a conductive layer from the other side may adjust the parallel capacitance.

According to another aspect of the invention, a surgical tip may contain a matching circuit or network. The surgical tip may comprise different geometries having different characteristic impedance. Additionally, due to variations in fabrication, any two similar tips may have slightly different characteristic impedances. Thus each tip may be individually configured using the matching circuit. The surgical tips may be attachable to a handpiece which receives electrical energy from a power source via a transmission line having characteristic impedances that match the impedance of the surgical tip to achieve substantially maximum power transfer.

According to another aspect of the invention, standing wave ratio may be monitored to determine if the system has encountered a failure or a limit.

According to another aspect of the invention, a capacitor and/or inductor, such as an electronically controlled capacitor and/or inductor may be used in tuning the circuit. In one embodiment, the capacitor and/or inductor value may be set at manufacturing as part of the impedance matching setting. In another embodiment, the matching circuit may contain a processor that monitors SWR and adjusts an electronically controlled capacitor and/or inductor to minimize SWR.

According to another aspect of the invention, a coaxial cable having a characteristic impedance may be used in tuning the circuit.

According to still another aspect of the invention, inductors, transformers, resistors, varactors, coaxial cables, and/or combinations thereof may be used in tuning the circuit.

These and other aspects of the present invention are realized in an impedance matching circuit as shown and described in the following figures and related description.

BRIEF DESCRIPTION OF THE DRAWINGS

Various embodiments of the present invention are shown and described in reference to the numbered drawings wherein:

FIG. 16A shows a close-up view of ferromagnetic coated conductor surgical tool tip with a loop geometry in accordance with one aspect of the present invention;

FIG. 16B shows a close-up view of a ferromagnetic coated conductor surgical tool tip with a generally square geometry in accordance with one aspect of the present invention;

FIG. 16C shows a close-up view of a ferromagnetic coated conductor surgical tool tip with a pointed geometry;

FIG. 16D shows a close-up view of a ferromagnetic coated conductor surgical tool tip with an asymmetrical loop geometry;

FIG. 16E shows a close-up view of a ferromagnetic coated conductor surgical tool tip with a hook geometry in which the concave portion may be used for therapeutic effect, including cutting;

FIG. 16F shows a close up view of a ferromagnetic coated conductor surgical tool tip with a hook geometry in which the convex portion may be used for therapeutic effect, including cutting;

FIG. 16G shows a close up view of a ferromagnetic coated conductor surgical tool tip with an angled geometry;

FIG. 22 shows an axial cross-sectional view of a single layer ferromagnetic coated conductor surgical tool in the ferromagnetic-coated region;

FIG. 23A shows a perspective view of a multi-layer ferromagnetic coated conductor surgical tool tip;

FIG. 23B shows a side cross-sectional view of a multi-layer ferromagnetic coated conductor surgical tool tip shown in 23A;

FIG. 24 shows an axial cross-section of the multi-layer ferromagnetic coated conductor surgical tool tip shown in FIG. 23A;

FIG. 27A shows a single edge ferromagnetic coated conductor surgical tip in accordance with one aspect of the invention;

FIG. 27B shows a double edge ferromagnetic coated conductor surgical tip;

FIG. 27C shows a three wire ferromagnetic coated conductor surgical tip;

FIG. 27D shows a receptacle for the tips shown in FIGS. 27A through 27C;

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Thus, multiple figures may be used to show a particular aspect of the invention. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1A:
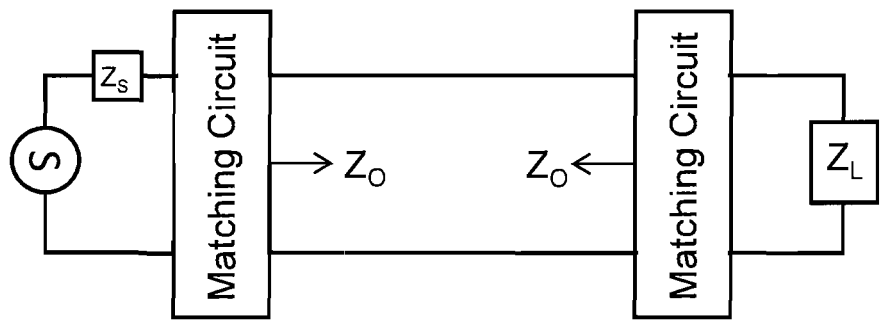
FIG. 1A shows a schematic of a circuit with two matching circuits in accordance with the prior art.
Figure 1B:
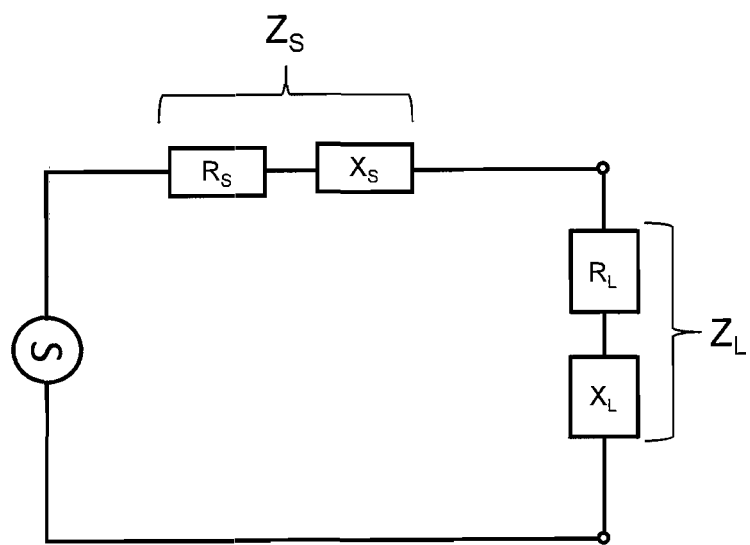
FIG. 1B shows a schematic of a circuit with a source impedance and load impedance in accordance with the prior art.
Figure 2:
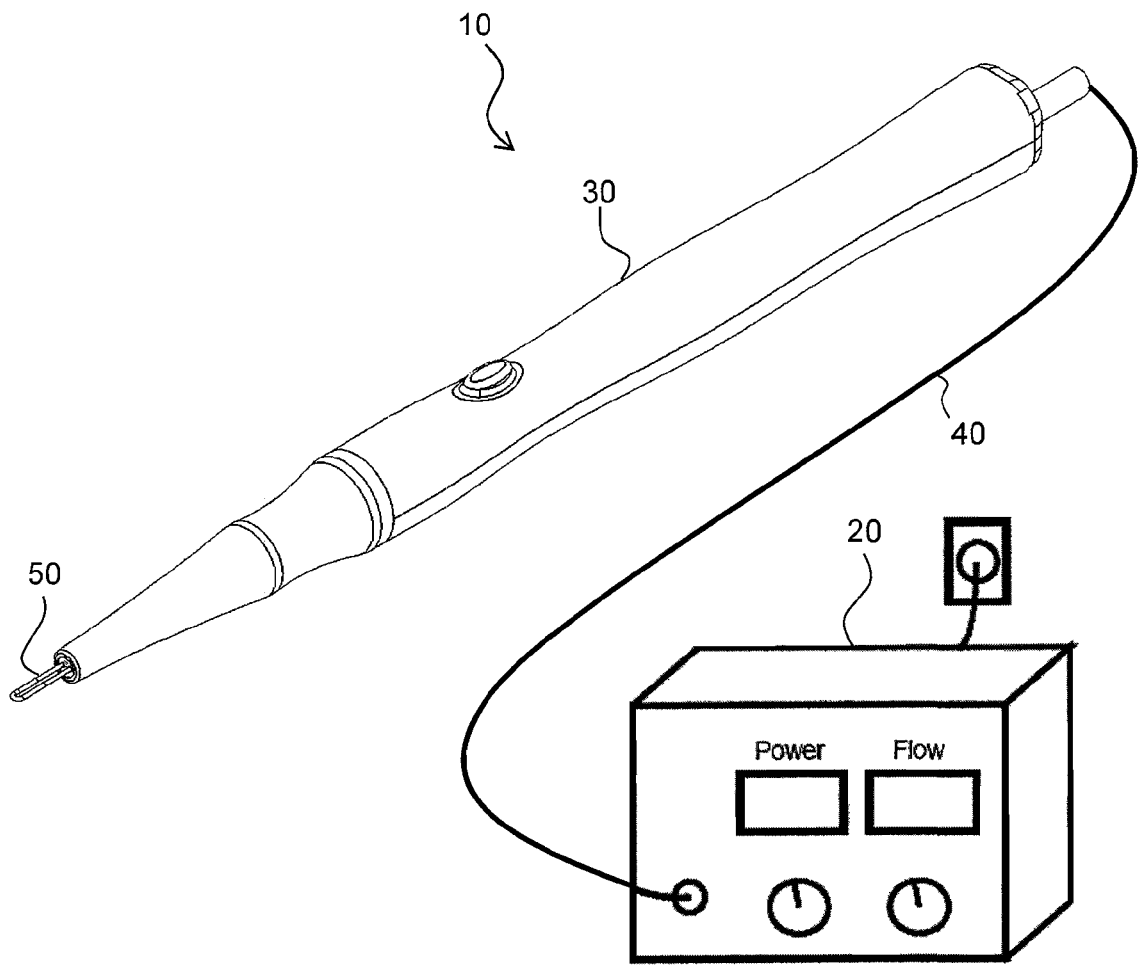
FIG. 2 shows a diagram of a surgical system in accordance with one aspect of the present invention.

Turning now to FIG. 2, a surgical system 10 is shown. A power source 20 provides power which is delivered to the surgical handpiece 30 through a transmission line 40. As maximum power transfer may be desired, the power source 20 may be impedance matched to the handpiece 30 equivalent load. More specifically, the power source 20 may be impedance matched to the transmission line 40, which may be impedance matched to the surgical handpiece 30. Therefore a matching circuit (also known as a network) may be used to match the power source to the load.

In the surgical handpiece shown, a thermal element 50, such as a ferromagnetic element, may form the active portion of the load. The thermal element may have little resistance. A matching circuit may be used to match the impedance of the power source to the load of the thermal element. Alternatively, inductors and/or coaxial cables (or other suitable components as explained in more detail below) may be used to complete a matching circuit with the thermal element. There are multiple thermal surgical tools which have been designed which may incorporate the principles of the present invention. Some such devices are disclosed in U.S. Publication Nos. 2010-0268207, 2010-0268214, 2010-0268208, 2010-0268209, 2010-0268215, 2010-0268205, 2010-0268210, 2010-0268212, 2010-0268213, 2010-0268211, 2010-0268216, 2010-0268206, all of which are expressly incorporated herein.

Figure 3:
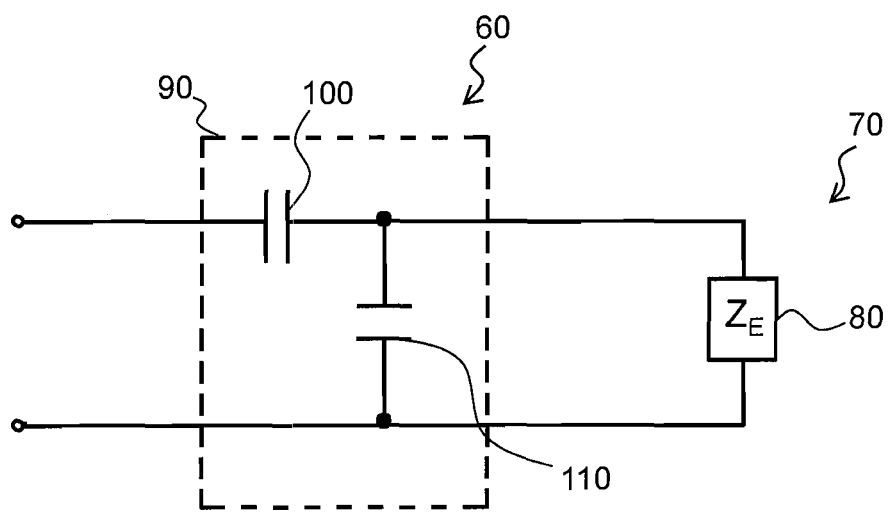
FIG. 3 shows a schematic of an equivalent circuit with a surgical element.

Turning now to FIG. 3, a schematic of an equivalent circuit 60 which may be used with a surgical element 70 is shown. The impedance of the surgical element 70 is designated as $Z_E$. In the case of some surgical elements 70 with some resistance and inductive reactance 80, the matching networks may be completed with a matching circuit 90. Each matching circuit may depend on the surgical element type, including chemical composition, geometry and physical properties. While a surgical element may be matched empirically, often times, a circuit may be monitored for a standing wave ratio (SWR) at a desired frequency, such as a voltage standing wave ratio (VSWR) and adjustments made to the matching network based on the SWR. According to one aspect of the invention, a surgical element 70 may be matched with a series capacitance 100 of between 10 pF and 300 pF and a parallel capacitance 110 of between 100 pF and 600 pF. More preferably, the element may be matched with a series capacitance of between 55 pF and 80 pF and a parallel capacitance of between 270 pF and 400 pF. The transmission line 40 (FIG. 2) may be a 50 ohm coaxial cable.

Figure 4:
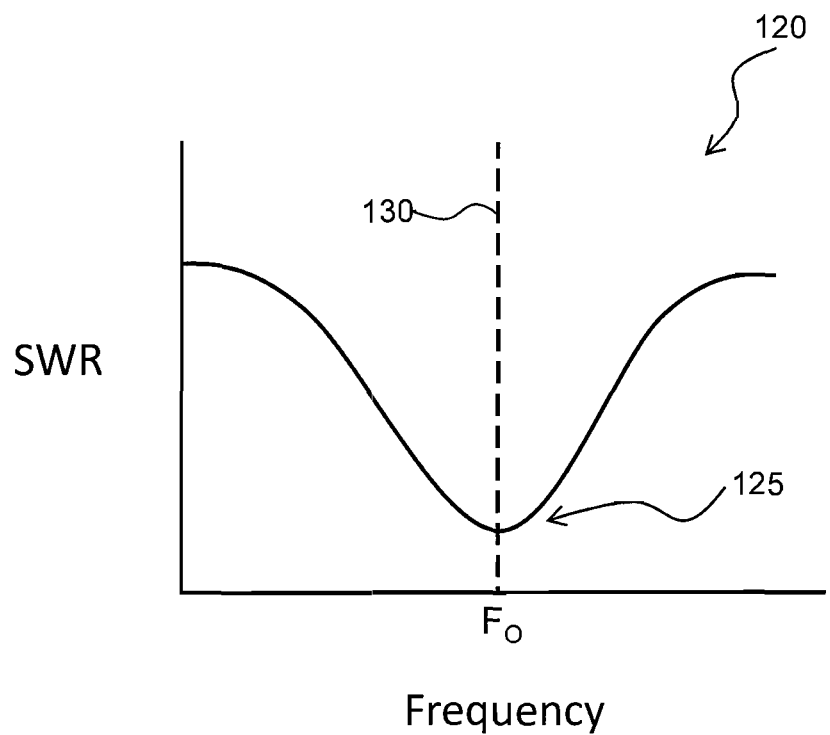
FIG. 4 shows a chart of standing wave ratio to frequency.

Turning now to FIG. 4, a chart 120 of standing wave ratio to frequency is shown. As SWR is minimized 125, power transfer is increased. In some cases, a SWR ratio of 1:1 may be desired with maximum power transfer at the target frequency ($F_0$) 130. Using the equivalent circuit of FIG. 3, the series capacitance 100 and parallel capacitance 110 may be altered to minimize the SWR.

Figure 5:
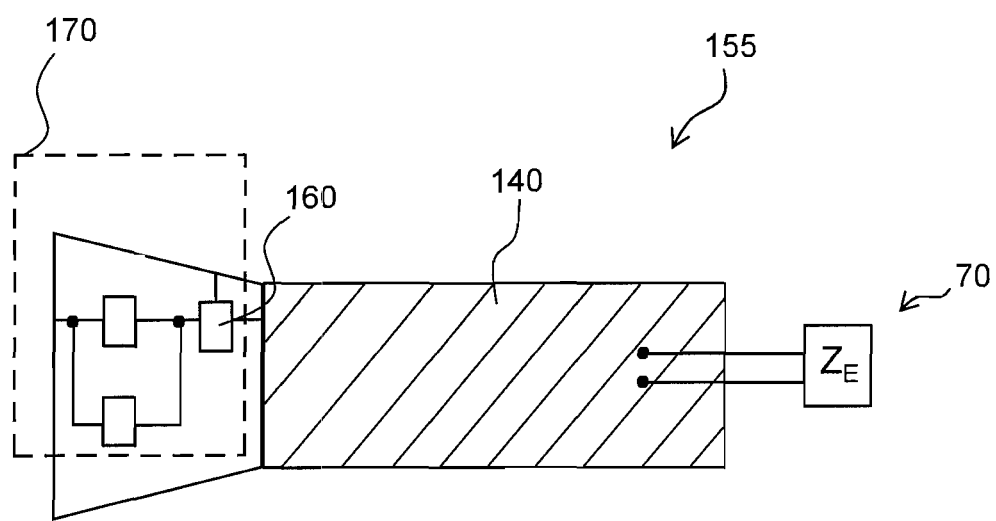
FIG. 5 shows a diagram of an unaltered circuit board matching circuit.
Figure 6A:
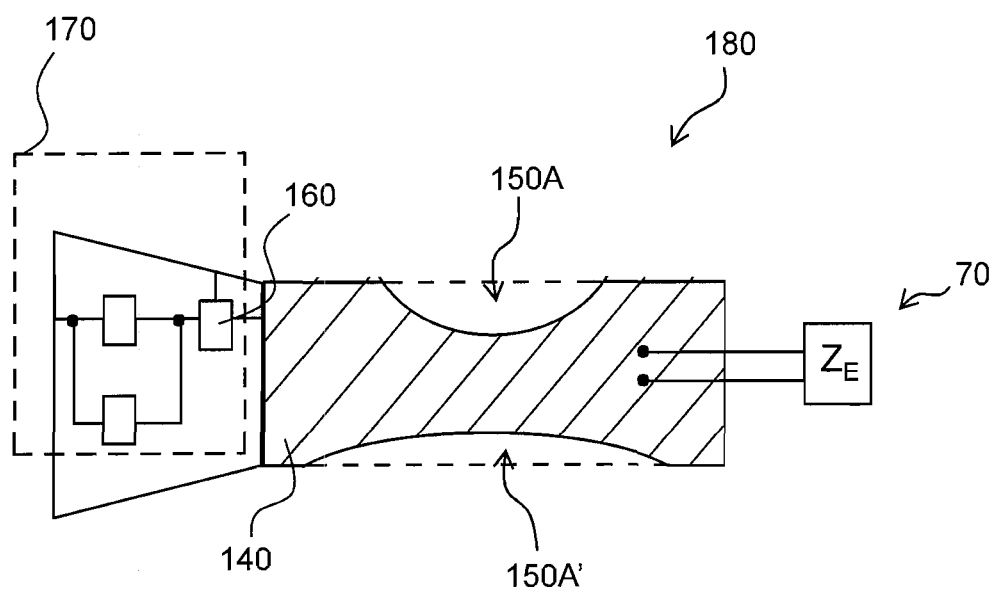
FIG. 6A shows a diagram of a single layer circuit board matching circuit.
Figure 6B:
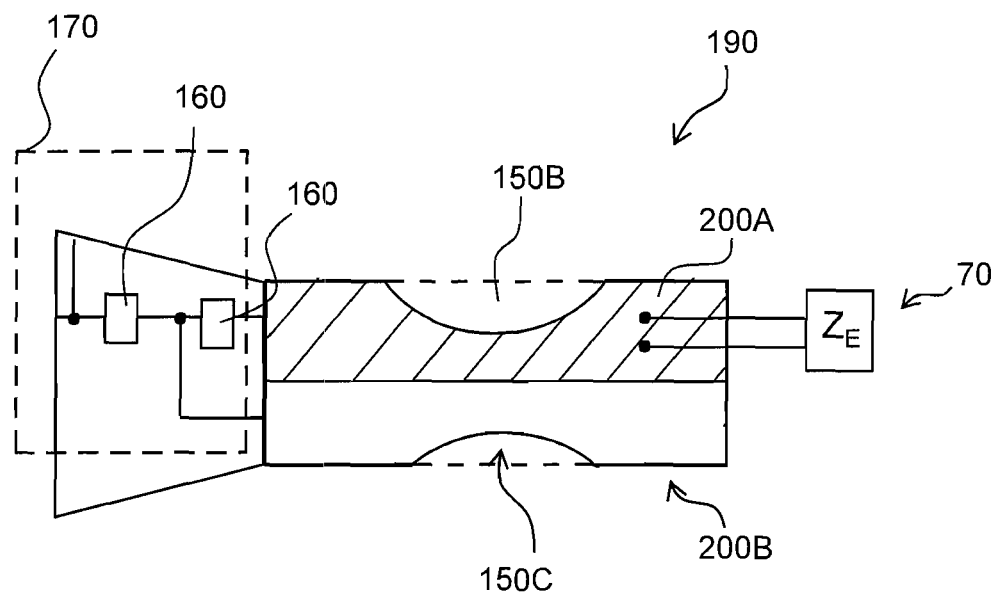
FIG. 6B shows a diagram of a two layer circuit board matching circuit.

Turning now to FIGS. 5, 6A and 6B, a circuit board, flex board, etc. may be used as part of the matching circuit. After an initial matching circuit and load are assembled, the matching circuit may be adjusted for better power transfer near the end of the manufacturing process. This allows the system to be individually adjusted for component and manufacturing tolerances.

More specifically, one or more layers of circuit board conductor 140 may be used as capacitors or other impedance matching circuit element. As cut out portions 150A (FIG. 6A), 150B (FIG. 6B), 150C (FIG. 6B) of the circuit board are removed, the capacitance (or other electrical characteristics) of the circuit board conductor layer may be reduced or increased. Thus, after being built, the circuit may be adjusted for some or all the manufacturing tolerances, and achieve a practically low SWR and better power transfer.

As a general note, although many of the embodiments described herein describe using capacitances to implement a matching circuit, other circuit elements may be used in addition to or instead of the referenced capacitors. Indeed, in this example embodiment, which has a primarily inductive load, capacitive tuning is readily applicable. In cases where the load looks capacitive, an inductive matching circuit may be appropriate. Any combination of reactive elements may be used to match one load to another.

Turning now specifically to FIG. 5, a diagram of an unaltered circuit board matching circuit is shown. At the end of manufacturing, a circuit board 155 may have one or more layers 140 of circuit board conductor 140, a fixed value portion 170 of the matching circuit, and a surgical element 70. A layer or layers of circuit board conductor 140, such as copper, may have intrinsic capacitance. The layer of conductor 140 may be placed in series or parallel with a fixed value capacitor 160 as part of a fixed value portion 170 of the matching circuit. The circuit board 155 may then be connected to a power source 20 (FIG. 2) and SWR monitored as the circuit board 155 is adjusted.

Turning now specifically to FIG. 6A, a diagram of a single plane circuit board 180 matching circuit is shown. The layer of conductor 140 may act as a variable capacitor. The layer of conductor 140 may be used to alter the effective capacitance of a series capacitor 100 or parallel capacitor 110 (see FIG. 3) as it may be placed in parallel or series with a fixed capacitor. By using the layer of conductor 140 with a fixed capacitance, the fixed capacitance may provide an initial value that may be effectively altered by the layer of conductor 140 to achieve a better SWR and consequently a better power transfer.

In the case of a single plane matching circuit, the capacitance of the layer of conductor 140 may be adjusted by removing portions 150A of the circuit board 180. SWR may be monitored while removing portions 150A of the circuit board 180. For example, SWR may be monitored by a manufacturing system. When the system detects a minimum or acceptable SWR, the system may cease cutting the circuit board 180. In other embodiments, the circuit board 180 may not be removed, but the layer of conductor 140 may be removed.

According to one aspect of the invention, the single plane circuit board 180 may be assembled such that electrical components, including the surgical element, are attached. The circuit board may then be connected to a power source 20 (FIG. 2). While SWR is monitored, a laser may remove portions of the layer of conductor 140, which may include portions 150A of the single plane circuit board 180. When an acceptable SWR is reached, the system may stop removing portions of the layer of conductor 140. The single plane circuit board 180 may then move to further assembly.

According to another aspect of the invention, the circuit board 180 may be used as a divider, such as in cooling applications. Therefore it may be desirable to cut longer portions 150A' of smaller width than portions 150A with larger width.

Turning now to FIG. 6B, a diagram of a two layer circuit board 190 matching circuit is shown. With a two layer circuit board 190, an upper layer 200A and lower layer 200B may be used to alter the effective capacitance of a series capacitor 100 and parallel capacitor 110 (see FIG. 3) as the upper layer 200A and lower layer 200B may be placed in parallel or series with a fixed capacitor. Thus, both the effective series capacitance 100 and effective parallel capacitance 110 may be adjusted.

SWR may be monitored as the upper layer 200A is adjusted by forming the cut-out portion 150B, and lower layer 200B may be adjusted by the cut-out portion 150C. When the SWR is acceptable or is near a minimum, the system may stop removing material from upper layer 200A and/or lower layer 200B. Thus, the upper layer 200A and lower layer 200B may be used to modify fixed capacitors 160.

Although embodiments of matching circuits are described which combine a circuit board conductor 140 with other discrete circuit elements (e.g., capacitors), other embodiments may be implemented which rely solely on circuit board conductors 140. Also, although embodiments of the circuit board conductor 140 are described as being implemented on a circuit board 150, other types of flexible or rigid circuit substrates may be used.

While circuit board layers or layers on a flex board have been discussed in FIGS. 5-6B, it should be recognized that it may be desirable to use multiple conductor layers in a multi-layer circuit board to create a single capacitance. For example, a conductor 140 acting as a capacitor may include an upper plate formed by a conductive circuit board layer, a dielectric formed by an insulating circuit board layer, and a lower plate formed by another conductive circuit board layer. Furthermore, it should be recognized that more than two planes or layers may be used in the circuit by providing areas that may be removed to adjust different planes/layers. In some cases, it may be desirable to have overlap in the planes, so that more than one capacitance may be altered by a single cut.

Figure 7:
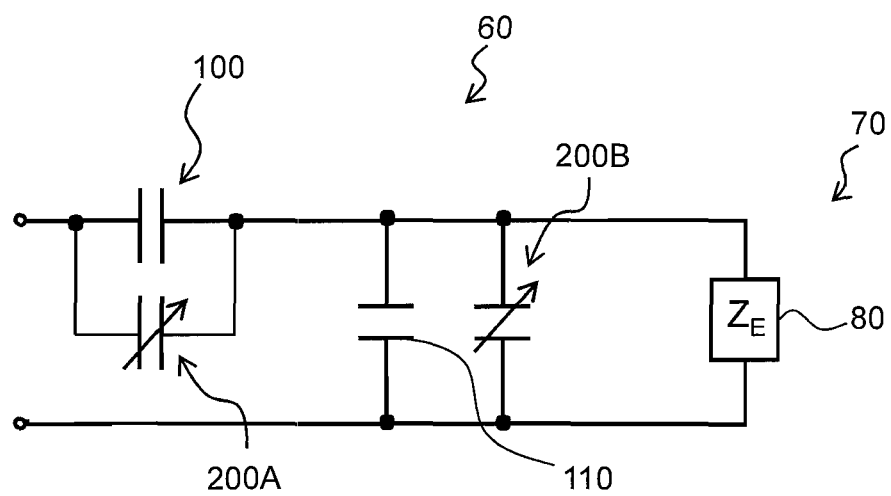
FIG. 7 shows an equivalent schematic of the circuit board matching circuit in 6B.

FIG. 7 shows a schematic of one embodiment of a circuit board matching circuit. Fixed capacitances, such as series capacitance 100 and parallel capacitance 110 may be altered by the capacitances of upper layer 200A and lower layer 200B. The capacitances allow the manufacturer to adjust the impedance matching circuit after the circuit has been constructed. As surgical element impedance 80 and fixed capacitances may have manufacturing tolerances, the circuit may be tuned for better power transfer from a power source 20 (FIG. 2) to surgical element 70. This ability to tune the circuits is similar, in some aspects, to using a variable capacitor. As such, the capacitances 150A that are adjusted by the manufacturer may be referred to as variable capacitances, although the variability is achieved through irreversible physical alterations.

Series capacitance 100 may be altered by the upper layer 200A variable capacitance. As the capacitors are in parallel, their effect is additive. Therefore series capacitance 100 may be a minimum value which may be added upon by upper layer 200A.

Similarly, parallel capacitance 110 may be altered by the lower layer 200B variable capacitance. As the capacitors are in parallel, their effect is additive. Therefore parallel capacitance 110 may be a minimum value which may be added upon by lower layer 200B.

It should be recognized that either plane may modify either series or parallel capacitance by adjusting the circuit layout. The upper layer 200A may instead modify the parallel capacitance 110, and the lower layer 200B may instead modify the series capacitance 100. Likewise, the layers 200A and 200B may be placed side by side or in any other desired configuration.

Figure 8A:
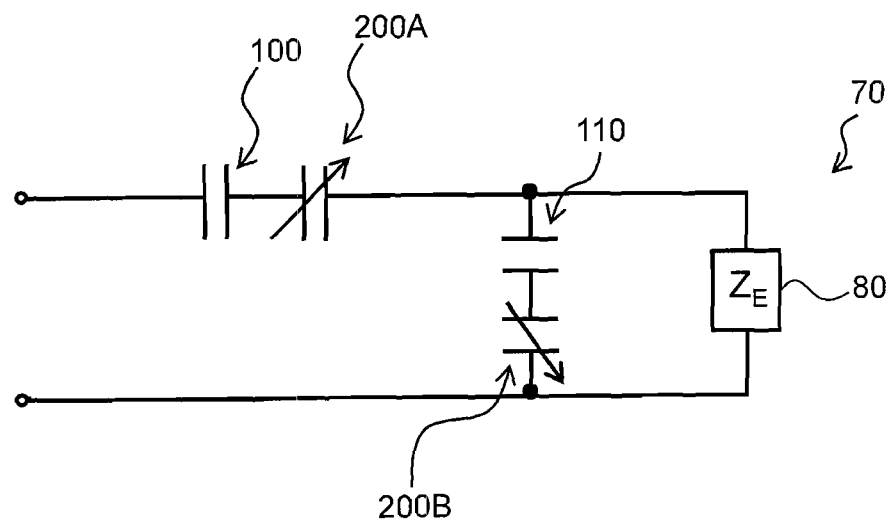
FIG. 8A shows an alternate schematic of a circuit board matching circuit.

Turning now to FIG. 8A, an alternate schematic of a circuit board matching circuit is shown. It should be recognized that the upper layer 200A and lower layer 200B may be installed in series or parallel with the series capacitance 100 and parallel capacitance 110. In the figure shown, the capacitances are related to their inverse such that the relation to the effective capacitance ($C_{eff}$) is $1/C_{eff}=1/C_{100}+1/C_{200A}$. Thus, the effective capacitance will be smaller than either of the capacitances in series. Therefore, the series capacitance 100 and/or the parallel capacitance 110 may be chosen as a maximum amount to be adjusted downward by the corresponding variable layer capacitance.

Figure 8B:
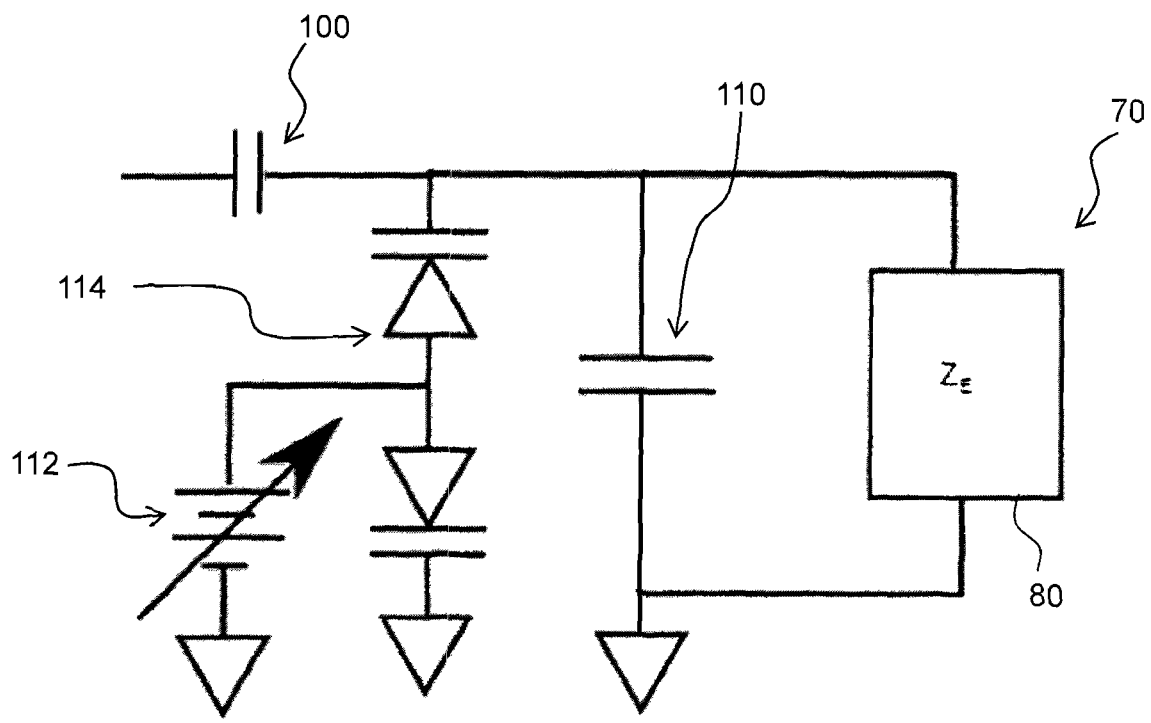
FIG. 8B shows another alternate schematic of a circuit board matching circuit with a varactor.

Turning now to FIG. 8B, a varactor diode may be used to adjust the apparent parallel capacitance 110 in a matching network. A variable voltage supply 112 may cause the varactor diodes 114 to increase or decrease their depletion region size, changing the functional capacitance of the devices, which in turn additively changes the total capacitance of parallel capacitor 110 and the varactor diodes 114. The voltage supply 112 may be a fixed reference from a voltage divider network or regulated supply, driven by a digital to analog converter, an operation amplifier, or any other mechanism especially those which may adjust the voltage as part of an open or closed feedback loop. It will also be apparent to those skilled in the art that series capacitor 100 can be adjusted by a similar manner. It will be further apparent to those skilled in the art that a varactor diode 114 may be substituted with a number of other types of devices such as rectifying diodes, which exhibit the same behavior as they are biased with an electric potential. Thus, to the extent that the variable voltage source is controlled to adjust based on operating characteristics of the surgical tip 70, the varactor diode 114 may provide for a self-tuning surgical tip.

Figure 9:
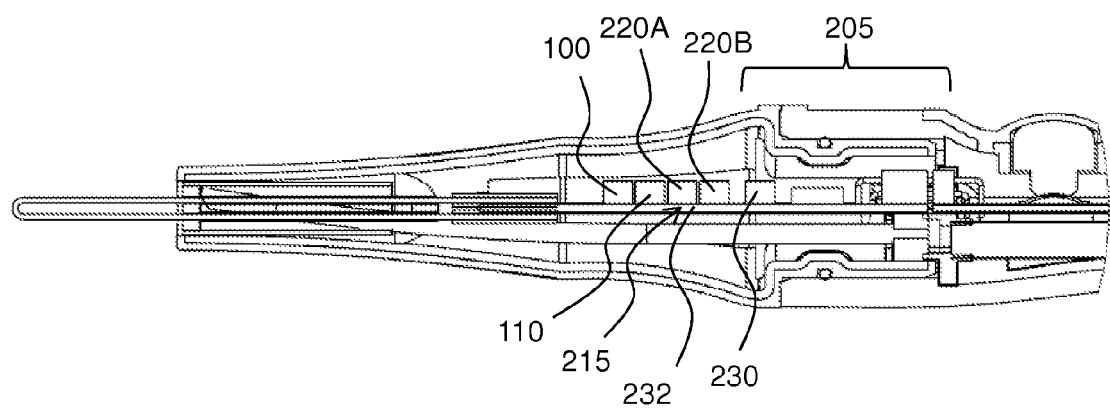
FIG. 9 shows a replaceable tip matching circuit and joint.

Turning now to FIG. 9, a replaceable tip with matching circuit 215 and joint 205 is shown. A replaceable tip with matching circuit 215 may be connected to a handle body through a joint 205. Similar to the circuit seen in FIG. 7, the matching circuit 215 may contain a series capacitance 100 and parallel capacitance 110. Electronically controlled capacitors 220A, 220B may be used to adjust the effective series and parallel capacitance for impedance matching.

The electronically controlled capacitor values 220A, 220B may be set at manufacturing. After assembly of the replaceable tip electronics, the replaceable tip may be connected to a power source 20 (FIG. 2). Electronically controlled capacitors may be adjusted until an acceptable SWR or near minimum SWR has been obtained. The electronically controlled capacitors may then have their settings stored with the matching circuit 215, as described in more detail.

Storing settings or controlling components of the matching circuit may be accomplished through multiple methods. According to one aspect of the invention, a processor 230 may store the settings in non-volatile memory. Alternatively, fuses may be used, such that by "blowing" a fuse, or rendering it inactive, a different setting is stored. According to another aspect, circuit traces may be joined, such that each joining of a trace causes a different setting to be stored.

In another embodiment, a processor 230 may monitor the SWR and adjust the electronically controlled capacitors. It may be desirable to have an active method of minimizing the SWR. By actively monitoring SWR, a system may be operable over more than a narrow frequency band. Thus, if different frequencies are desirable in different instances, an operator may choose the most effective frequency and the matching circuit 215 may automatically match the new impedance of the source, line and/or load.

According to one aspect of the present invention, the sensor 232 may monitor SWR and the information gathered by the sensor 232 may be used to adjust controllable capacitors, controllable inductors, controllable resistors, and/or other controllable components which might make up the matching circuit 215 according to principles discussed herein. In some embodiments, a matching circuit may be made more useful over a larger range of devices by including variable inductance, capacitance and/or resistance in the matching circuit. The matching circuit may thus be able to accommodate more surgical elements and/or more frequencies.

The sensor 232 may monitor SWR or another indicator which provides information regarding the efficiency of power transfer from a power source to the surgical instrument. Thus, when the indicator, such as SWR, suggests that power is being lost in transmission to the surgical instrument, the circuit may be adjusted so that power transfer is improved or maximized. In the case of SWR, the matching circuit may attempt to make adjustments to achieve SWR of 1:1 that may provide a desired response of better power transfer to the surgical element. The circuit may use variable inductors, capacitors, transformers, transmission lines, resistors, and/or combinations of the foregoing to accomplish this goal.

The overall goal of the present invention is to provide for tuning of a thermal surgical instrument by transforming the impedance of a load, for example the load of a thermal element such as a ferromagnetic tip, to match that of a transmission line connecting a power source to the thermal element. For example, the transmission line which carries the RF current from a power source to a surgical handpiece may be 50 ohms. The thermal element, such as a ferromagnetic tip may have a load of, for example, 2+i18 ohms. To transform the inductive load of the thermal element to a 50+i0.0 ohm load to match the characteristic impedance of the transmission line, components such as capacitors, coaxial cables, varactors, and sometimes more inductors may be used.

A Smith chart may be used to determine which components will make up the matching circuit. The Smith chart is plotted on the complex reflection coefficient plane in two dimensions and may be scaled in normalized impedance. The Smith chart has circumferential scaling in wavelengths and degrees. The wavelengths scale is used in distributed component problems and represents the distance measured along the transmission line connected between the generator or source and the load to the point under consideration. The degrees scale represents the angle of the voltage reflection coefficient at that point.

For example a Smith chart having a normalized impedance of 50 ohms may be used to design a matching circuit for matching the impedance of a load with the impedance of a transmission line having a characteristic impedance of 50 ohms. FIGS. 10A-10D show several examples of how one might transform the impedance of the load of a surgical tip of the present invention. It will be appreciated that there are a variety methods, other than using a Smith chart, which may be used to design a matching circuit of the present invention. Furthermore, those skilled in the art will appreciate that examples shown in FIGS. 10A-10D are not exhaustive of how the load may be matched to the characteristic impedance of a transmission line.

Figure 10A:
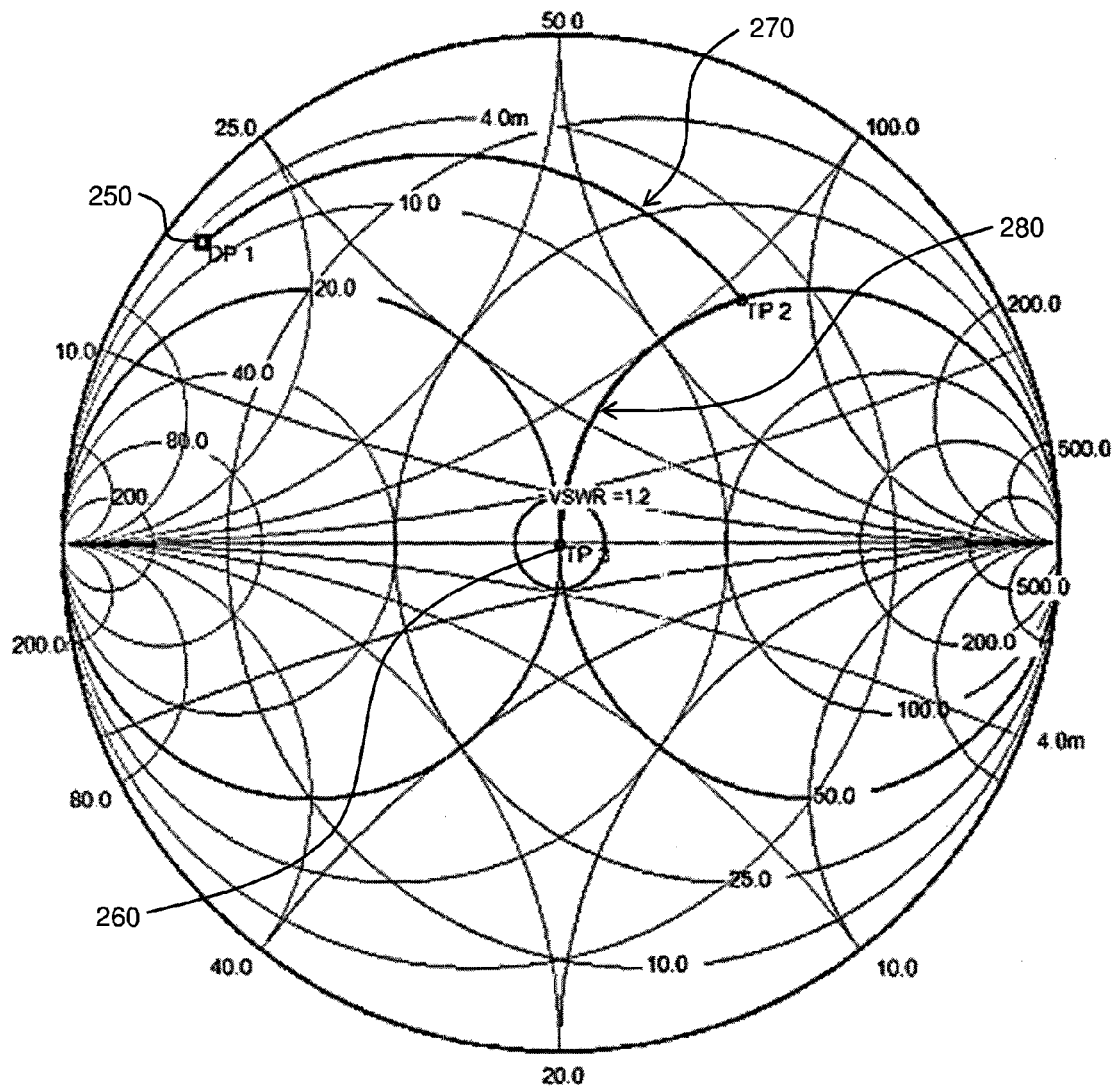
FIG. 10A shows a Smith chart and schematic for matching the load of a surgical tip with a source impedance using capacitors.
Figure 10A:
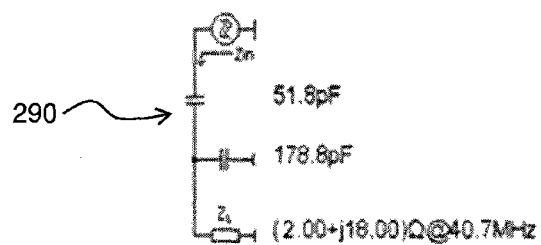

Turning now to FIG. 10A, there is shown a Smith chart having a normalized impedance of 50 ohms for designing a matching circuit for a transmission line having a characteristic impedance of 50 ohms. It will be appreciated that transmission lines having different characteristic impedance values may be used with a thermal surgical instrument of the present invention, however, for ease of illustration the Smith chart discussed herein all have normalized impedance of 50 ohms. FIG. 10A illustrates how capacitors may be used to transform the load of a surgical tip 250 to match the source impedance of a transmission line 260. The load of the surgical tip 250 is 2+i18 ohms. Capacitors connected in series and parallel may be used to transform the load of the surgical to about 50+i0.0 ohms. The Smith chart may be used to determine the proper capacitance to match the load 250 to the characteristic impedance of the transmission line. For example, the load 250 may be matched using a series capacitance 280 of about 52 pF and a parallel capacitance 270 of about 179 pF. A schematic 290 of the matching circuit is also shown in FIG. 10A.

Figure 10B:
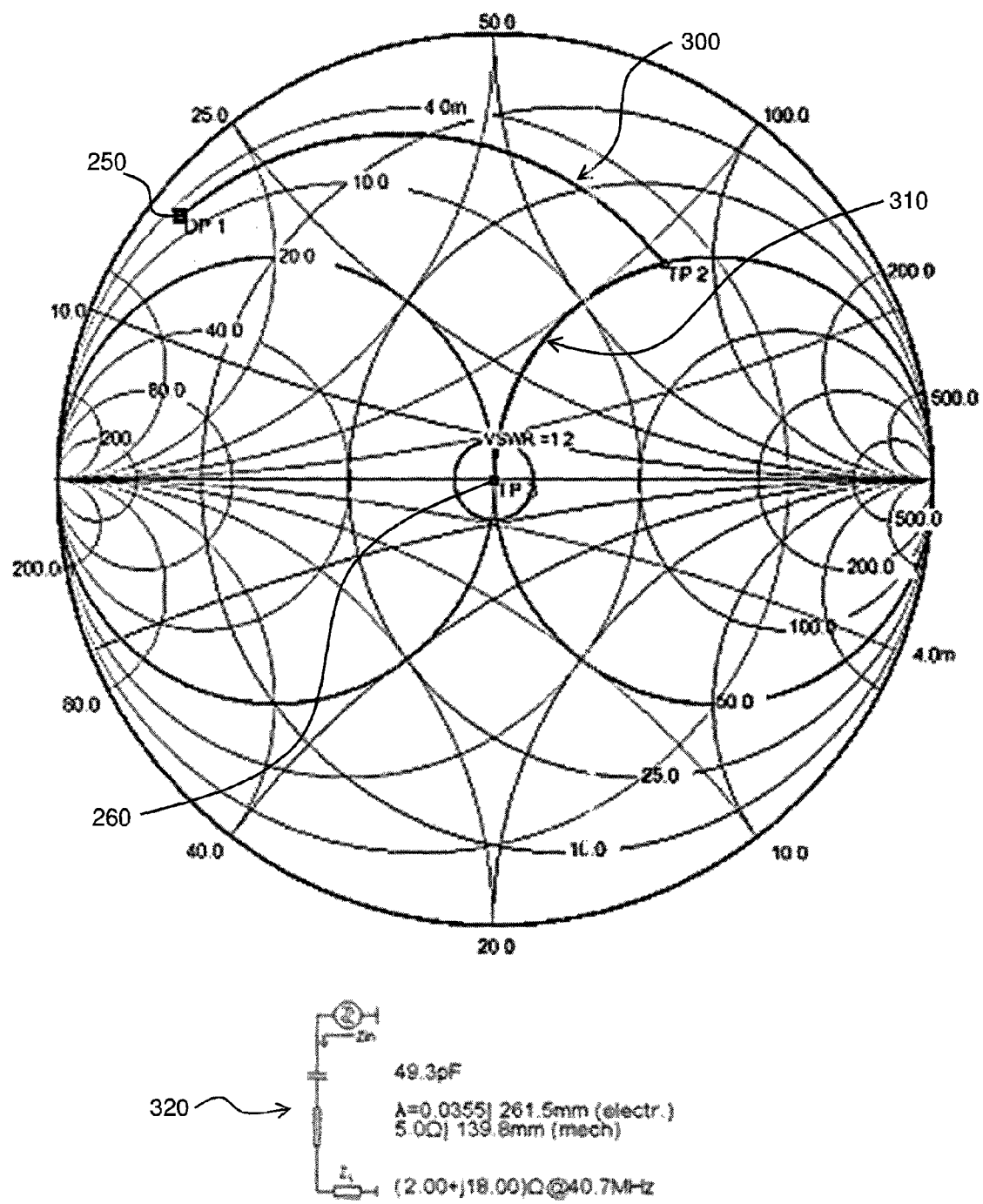
FIG. 10B shows a Smith chart and schematic for matching the load of a surgical tip with a source impedance using a capacitor and a coaxial cable.

FIG. 10B illustrates how a length of coaxial cable and capacitors may be used match the load of a surgical tip 250 with a source impedance 260. A series capacitance 280 of about 49 pF and a coaxial cable 270 may be used to transform the load 2+i18 of the surgical tip 250 to about 50+i0.0 so that it substantially matches the source impedance 260. A schematic 320 of such a matching circuit is also shown in FIG. 10B.

Figure 10C:
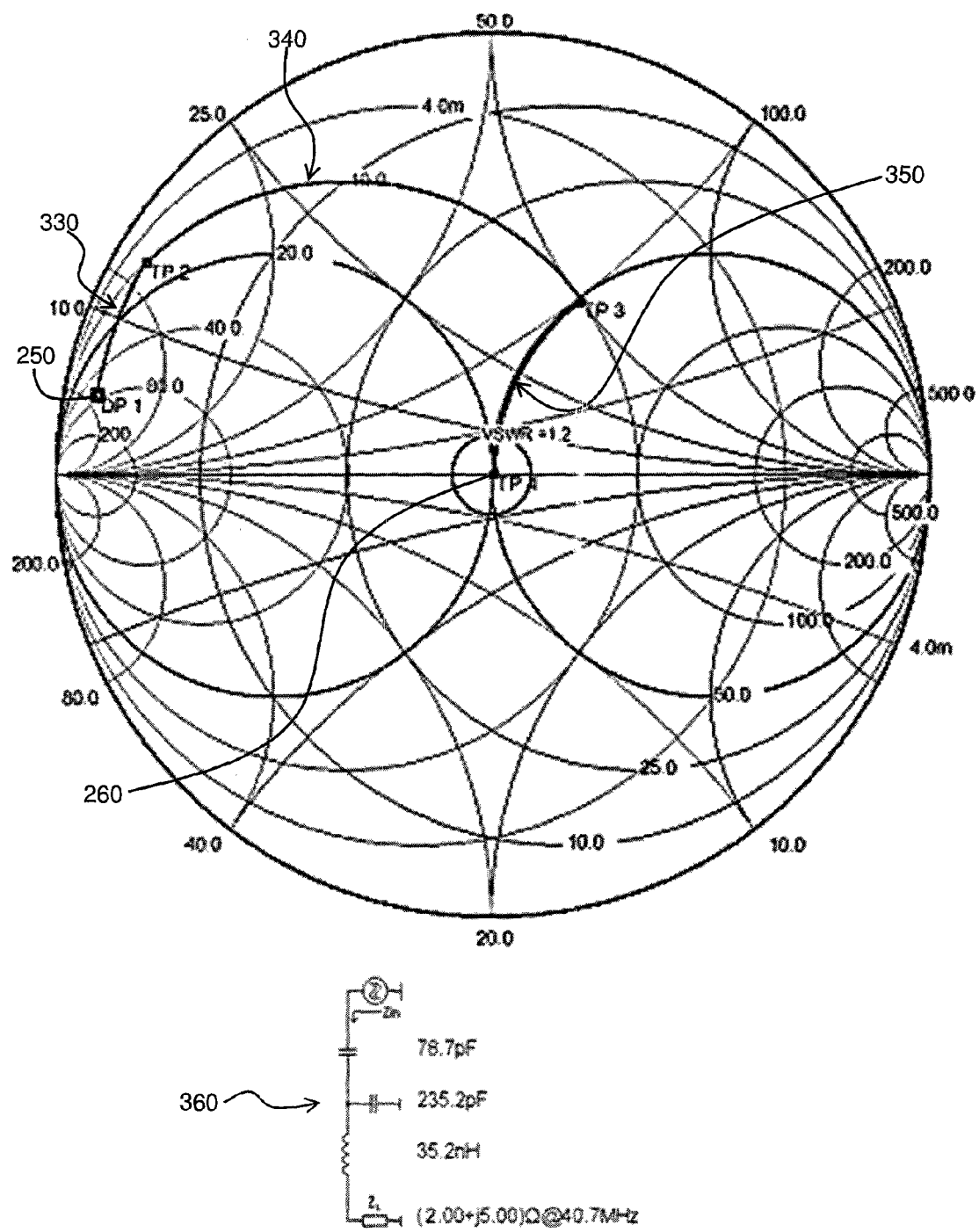
FIG. 10C shows a Smith chart and schematic for matching the load of a surgical tip with a source impedance using capacitors and an inductor.

FIG. 10C illustrates how capacitors and inductors may be used match the load of a surgical tip 250 with a source impedance 260. A series capacitance 350 of about 79 pF, a parallel capacitance 340 of about 235 pF, and an inductance 330 of about 35 nH may be used to transform the load 2+i5 of the surgical tip 250 to about 50+i0.0 so that it substantially matches the source impedance 260. The matching circuit of FIG. 10C may be particularly useful with surgical tips which have very low impedance. A schematic 360 of such a matching circuit is also shown in FIG. 10C.

Figure 10D:
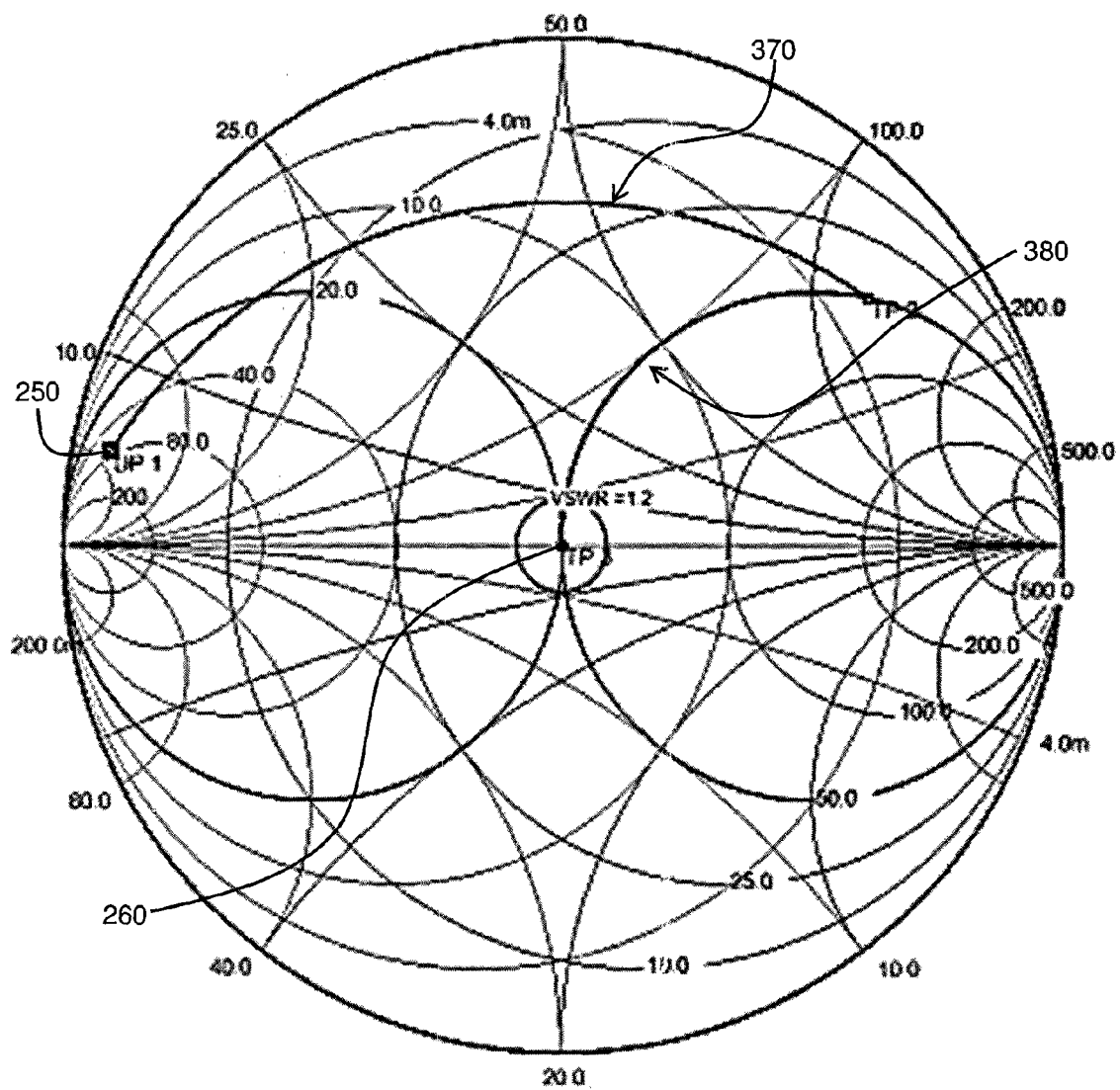
FIG. 10D shows a Smith chart and schematic for matching the load of a surgical tip with a source impedance using a capacitor and transformer.
Figure 10D:
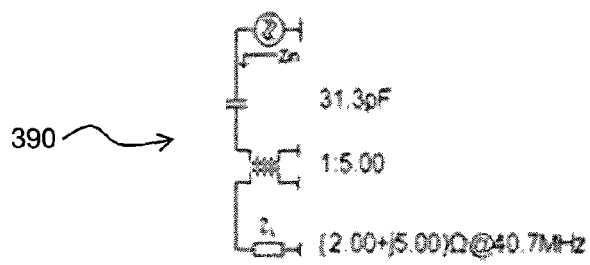
Figure 11A:
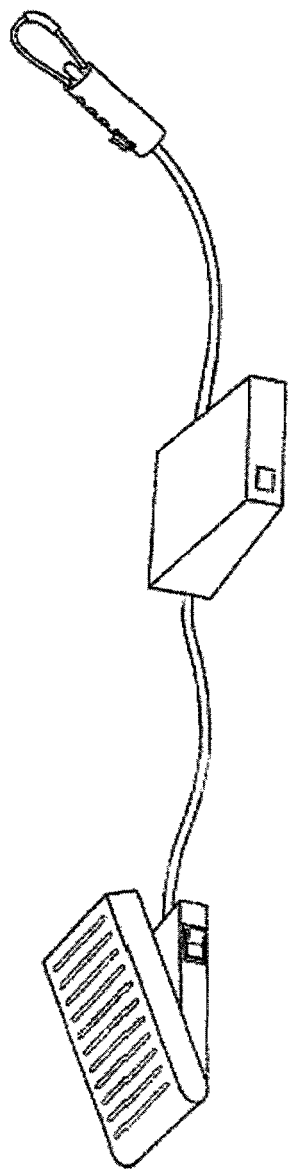
FIG. 11A shows a perspective view of a thermal surgical tool system.
Figure 11B:
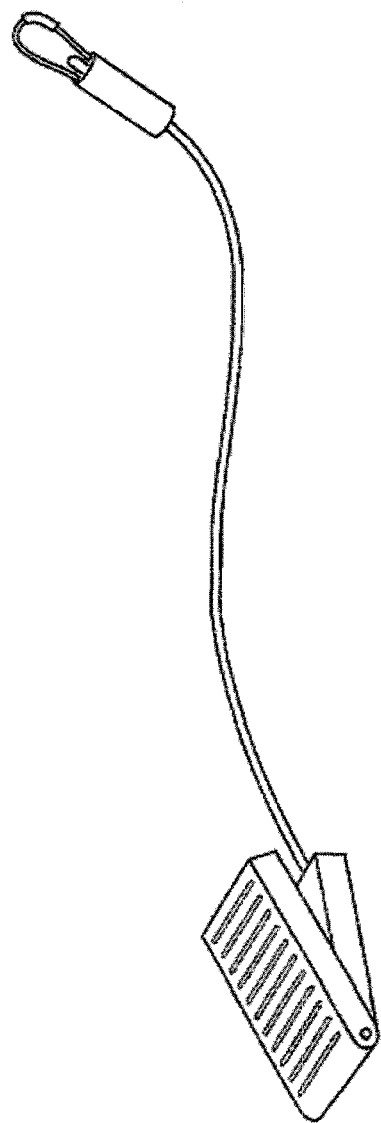
FIG. 11B shows a perspective view of an alternate embodiment of a thermal surgical tool system.
Figure 12:
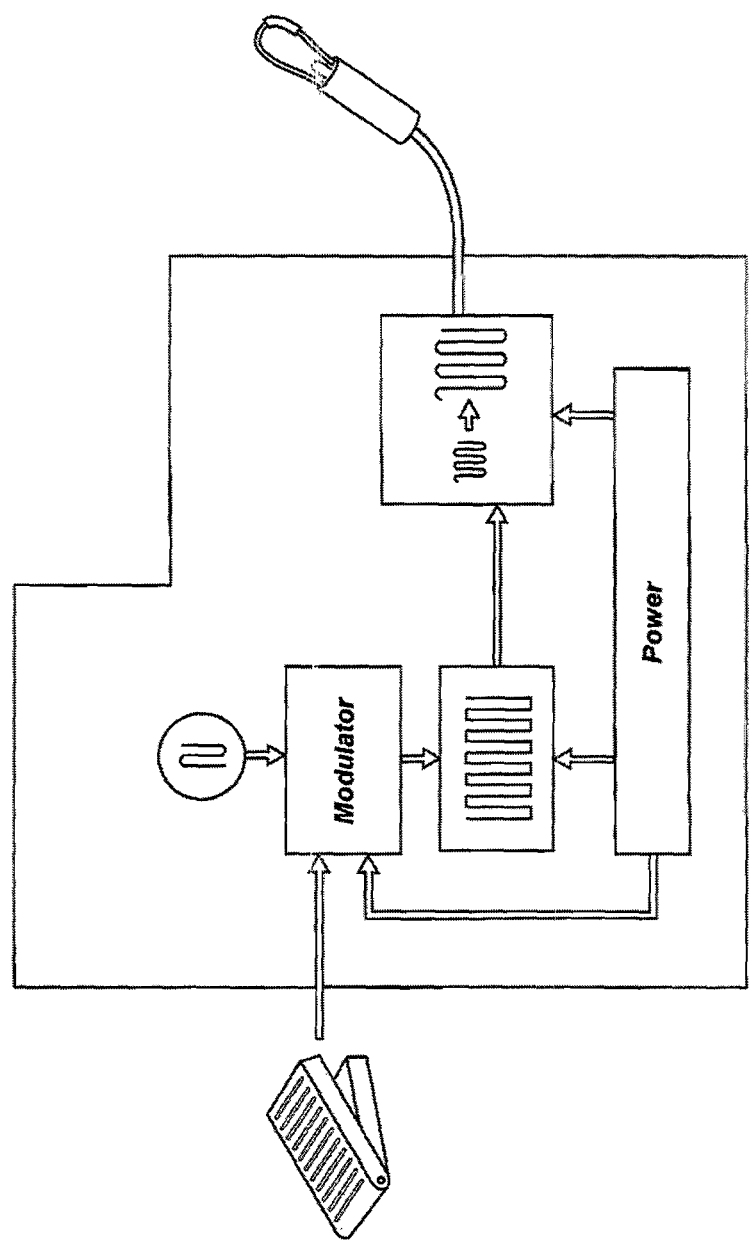
FIG. 12 shows a diagram of a thermal surgical tool system.

FIG. 10D illustrates how a capacitor and transformer may be used to match the load of a surgical tip 250 with a source impedance 260. A series capacitance 380 of about 31 pF and a transformer having a primary to secondary turn ratio of 1:5.00 (represented by reference numeral 370) may be used to transform the load 2+i5 of the surgical tip 250 to about 50+i0.0 so that it substantially matches the source impedance 260. A schematic 390 of such a matching circuit is also shown in FIG. 10D.

FIGS. 11A to 42 show various embodiments of surgical elements and handpieces that may benefit from an impedance matching circuit using the techniques and construction described above.

Figure 13A:
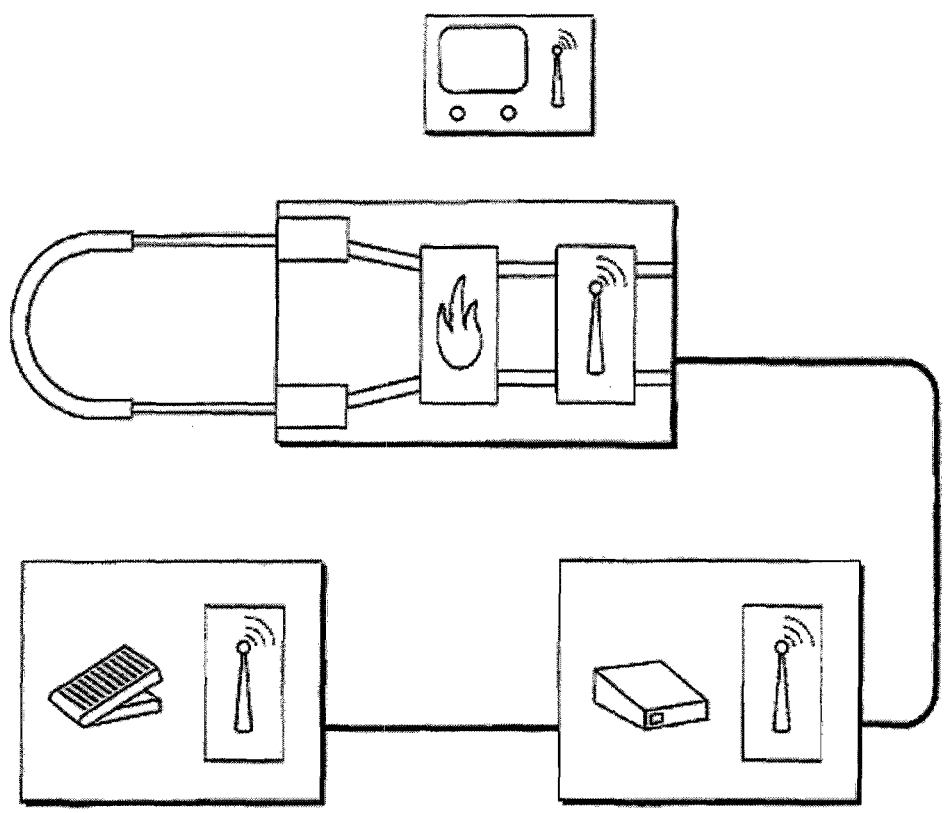
FIG. 13A shows a thermal surgical tool system with heat prevention terminals, heat sink, and wireless communication devices.
Figure 13B:
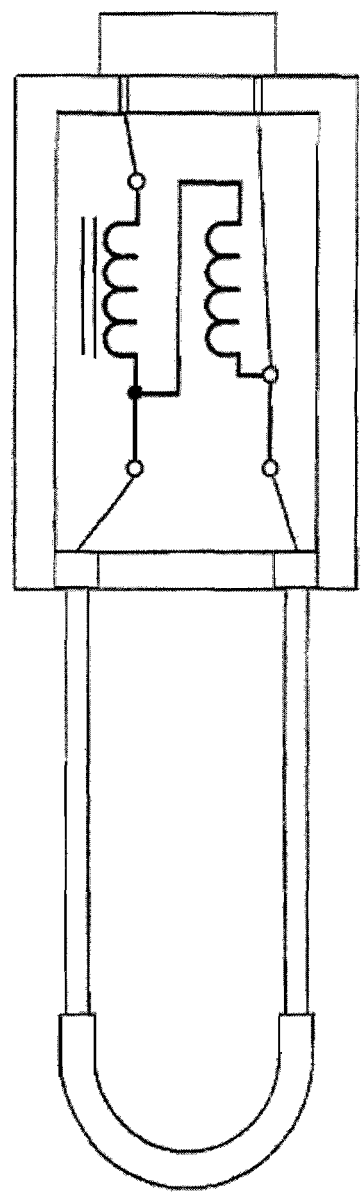
FIG. 13B shows a thermal surgical tool system with an impedance matching network.
Figure 14:
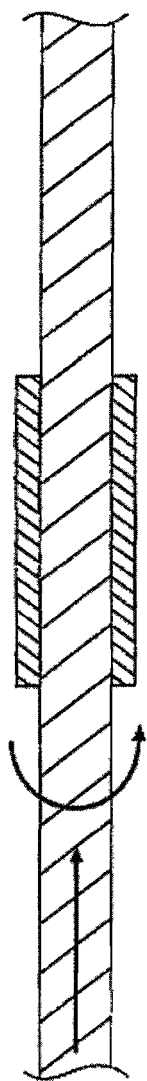
FIG. 14 shows a close-up, side cross-sectional view of a single layer ferromagnetic coated conductor tip in accordance with one aspect of the present invention.
Figure 15:
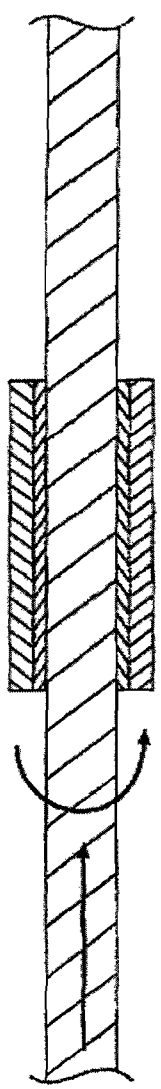
FIG. 15 shows a close-up, side cross-sectional view of a single layer ferromagnetic coated conductor tip with a thermal insulator in accordance with one aspect of the present invention.
Figure 17:
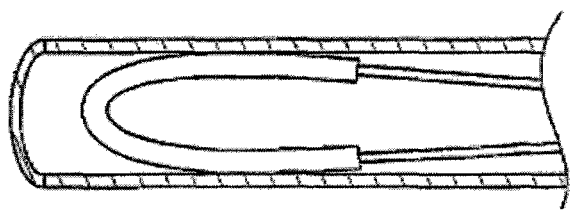
FIG. 17 shows a cut-away view of a retracted snare.
Figure 18A:
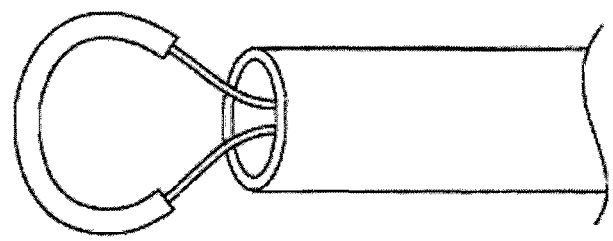
FIG. 18A shows a side view of an extended snare.
Figure 18B:
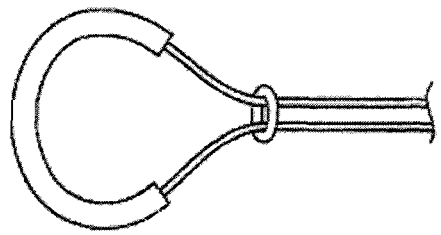
FIG. 18B shows an alternate embodiment of an extended snare.
Figure 19A:
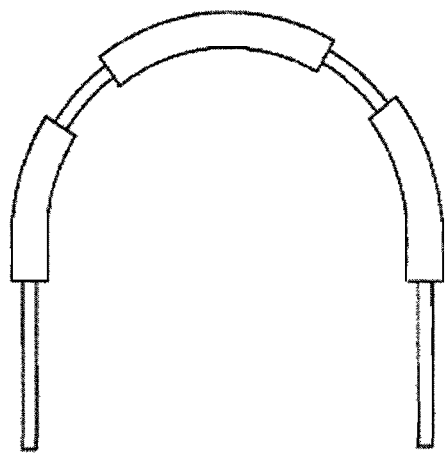
FIG. 19A shows a close-up view of a ferromagnetic coated conductor surgical tool with a loop geometry and array of coatings.
Figure 19B:
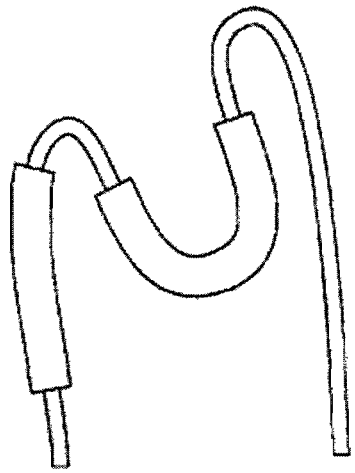
FIG. 19B shows a close up view of a ferromagnetic coated conductor surgical tool with an alternate hook geometry and array of coatings.
Figure 20:
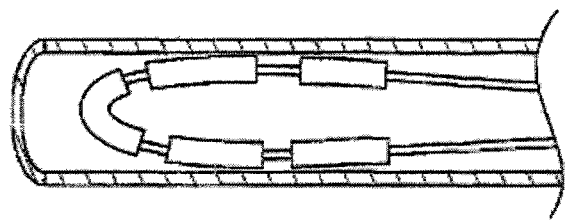
FIG. 20 shows a cut-away view of a retracted snare with an array of coatings.
Figure 21:
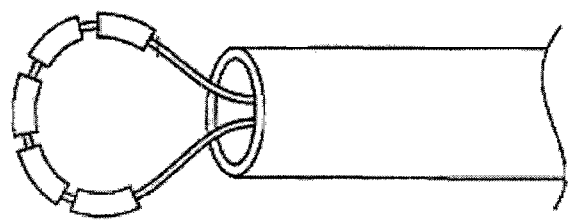
FIG. 21 shows a side view of an extended snare with a array of coatings.
Figure 25:
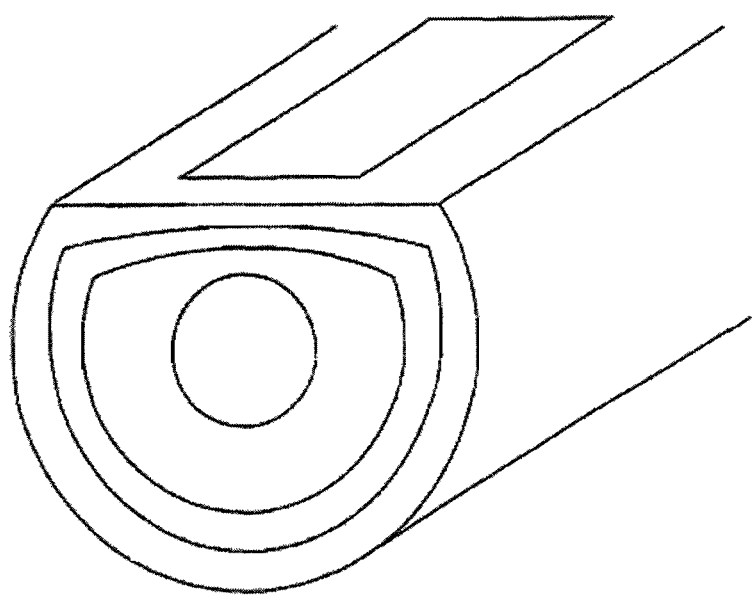
FIG. 25 shows a cross-sectional view of a flattened side cylindrical geometry ferromagnetic coated conductor showing electromagnetic lines of flux in accordance with one aspect of the present invention.
Figure 26:
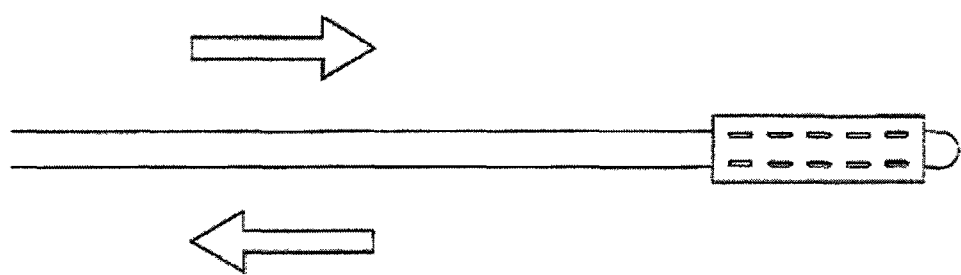
FIG. 26 shows a closed conductor tip in accordance with another aspect of the present invention.
Figure 28A:
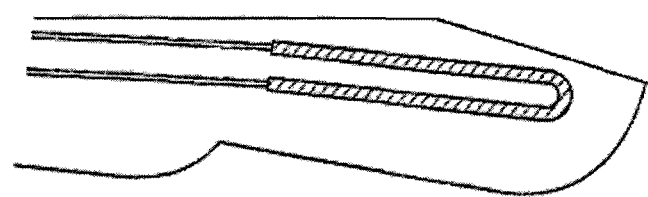
FIG. 28A shows a normally cold cutting scalpel with alternate inductive ferromagnetic thermal function.
Figure 28B:
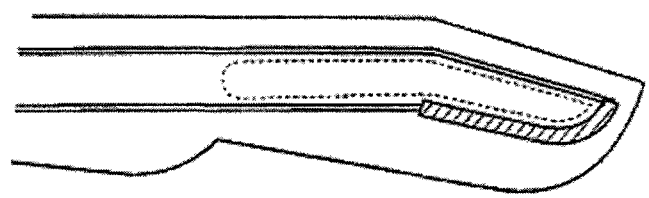
FIG. 28B shows an alternate embodiment of a normally cold cutting scalpel with alternate inductive ferromagnetic thermal function.
Figure 29A:
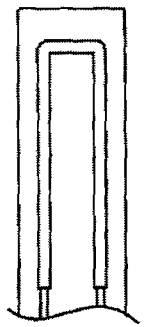
FIG. 29A shows a thermal surgical tool with a spatula shaped geometry.
Figure 29B:
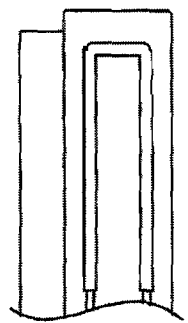
FIG. 29B shows a thermal surgical tool with a spatula shaped geometry in a forceps configuration.
Figure 29C:
FIG. 29C shows a top view of the thermal surgical tool of FIG. 29A with the ferromagnetic coated conductor upon the primary geometry.
Figure 29D:
FIG. 29D shows a top view of the thermal surgical tool of FIG. 29A with the ferromagnetic coated conductor embedded within the primary geometry.
Figure 30A:
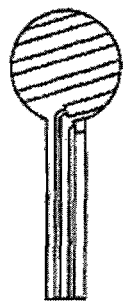
FIG. 30A shows a thermal surgical tool with a ball shaped geometry and horizontal winding.
Figure 30B:
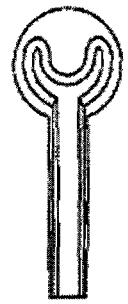
FIG. 30B shows an alternate embodiment of a thermal surgical tool with a ball shaped geometry and horseshoe configuration.
Figure 30C:
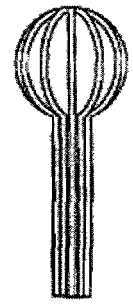
FIG. 30C shows an alternate embodiment of a thermal surgical tool with a ball shaped geometry and vertical orientation.
Figure 31A:
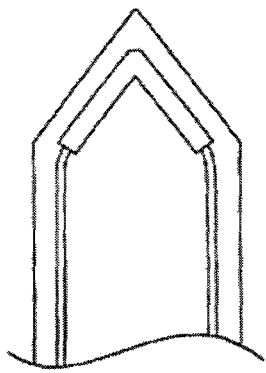
FIG. 31A shows a thermal surgical tool with a pointed geometry.
Figure 31B:
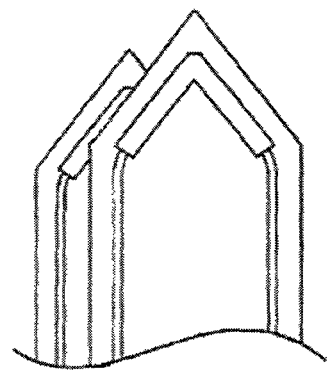
FIG. 31B shows a thermal surgical tool with a pointed geometry in a forceps configuration.
Figure 31C:
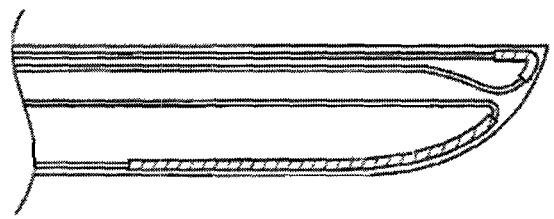
FIG. 31C shows a thermal surgical tool having two different activateable thermal zones.
Figure 32A:
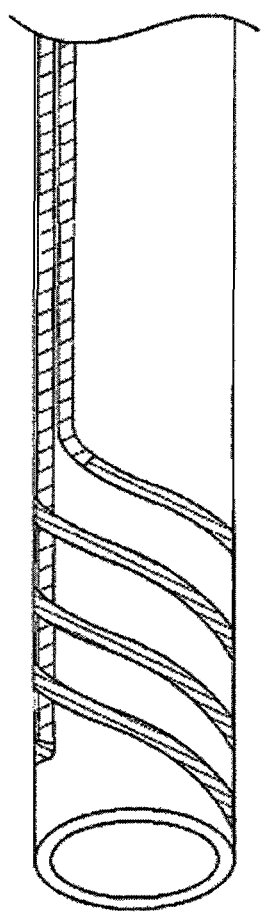
FIG. 32A shows a perspective view of a catheter having a coil of ferromagnetic coated conductor disposed around the tip of the catheter.
Figure 32B:
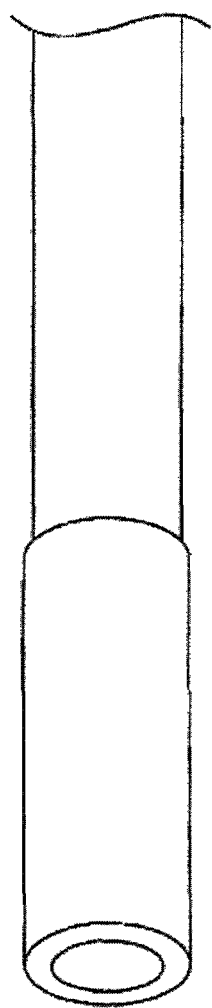
FIG. 32B shows a perspective view of a ferromagnetic coated conductor surgical catheter tip.
Figure 33:
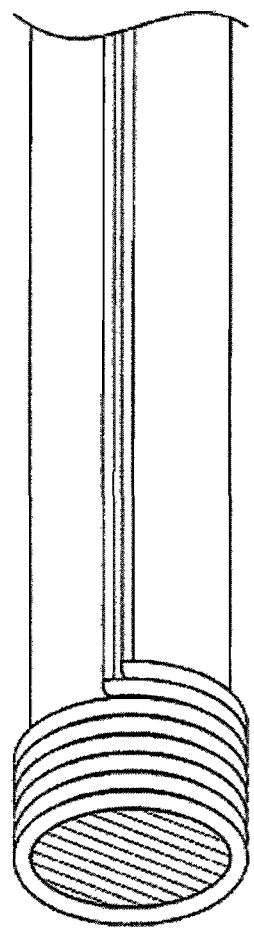
FIG. 33 shows a side view of an alternate embodiment of an ferromagnetic coated conductor surgical catheter tip.
Figure 34:
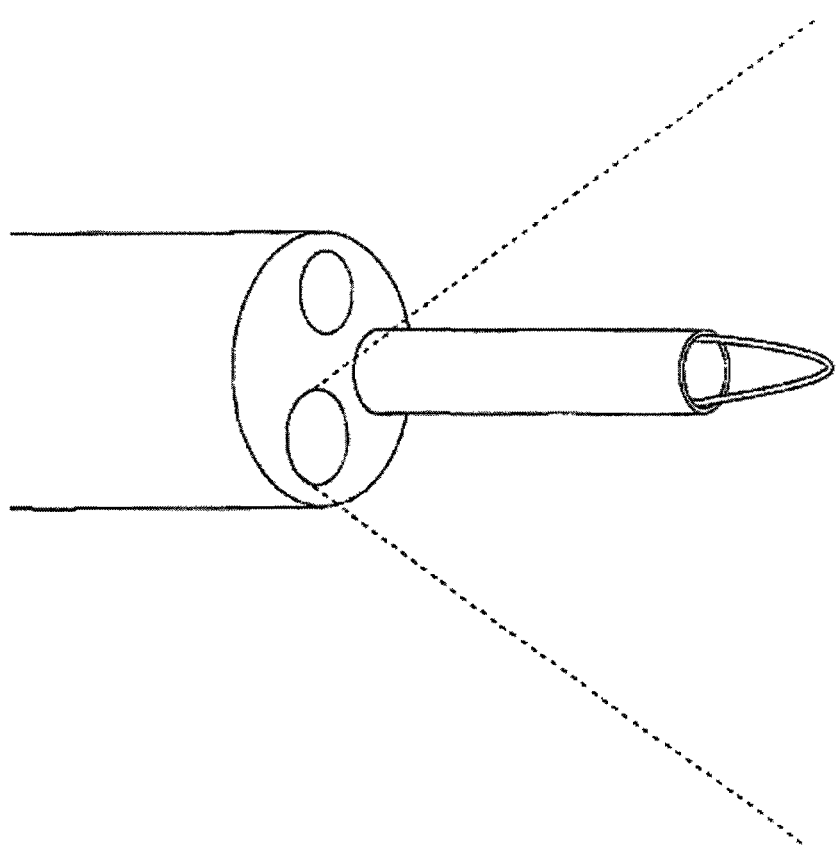
FIG. 34 shows an alternate embodiment of a ferromagnetic coated conductor surgical tip disposed within an endoscope.
Figure 35:
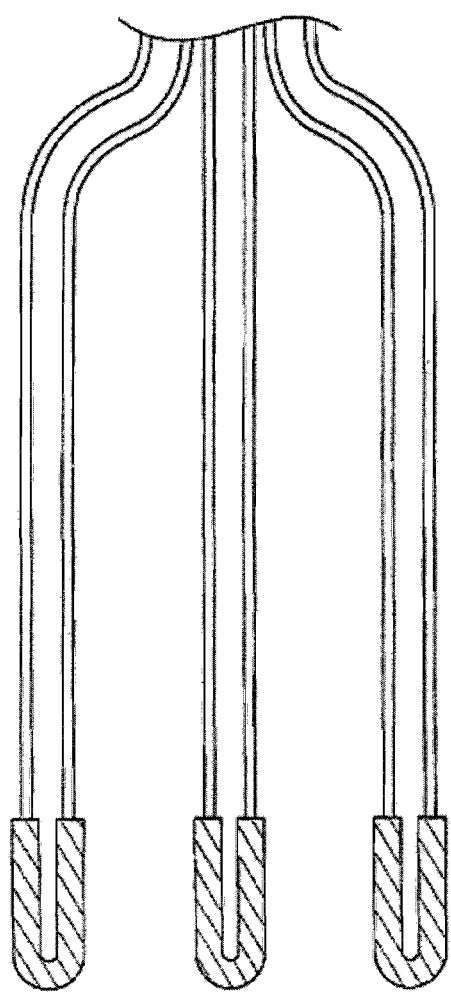
FIG. 35 shows a tissue ablation tool.
Figure 36:
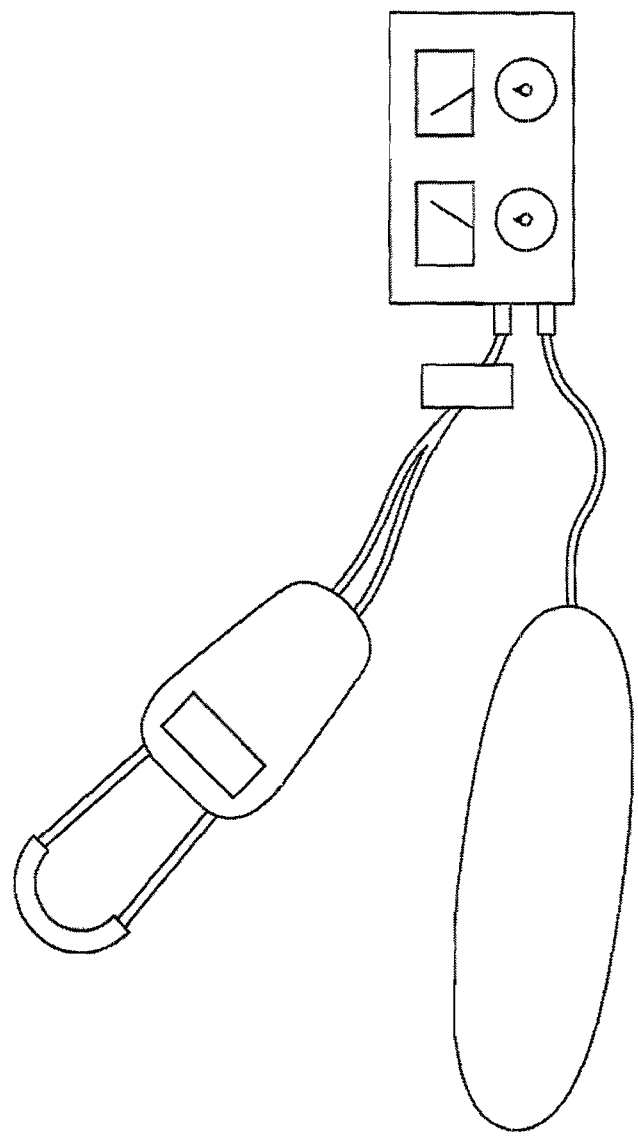
FIG. 36 shows a multi-mode surgical tool with monopolar and thermal modalities.
Figure 37A:
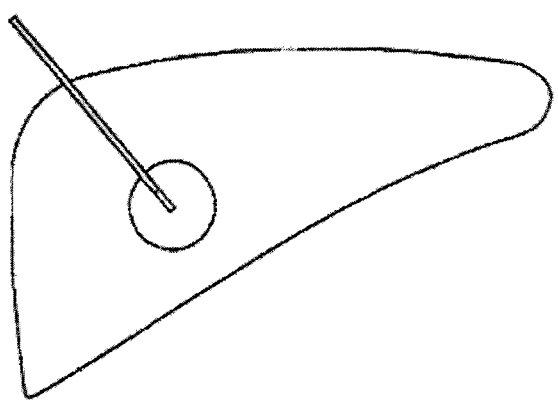
FIG. 37A shows a multi-mode tissue ablation tool within a metastasis in tissue, such as in a liver.
Figure 37B:
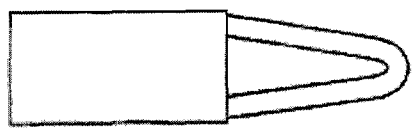
FIG. 37B shows a close-up the ablating probe of FIG. 37A.
Figure 37C:
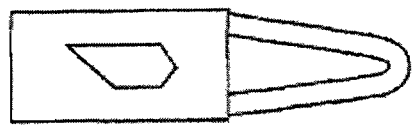
FIG. 37C shows a close-up of an ablating probe with a sensor.
Figure 37D:
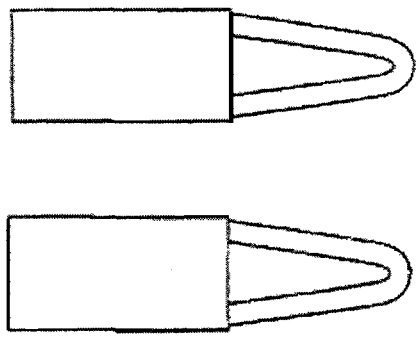
FIG. 37D shows a close-up of a multiple tip ablating probe.
Figure 38:
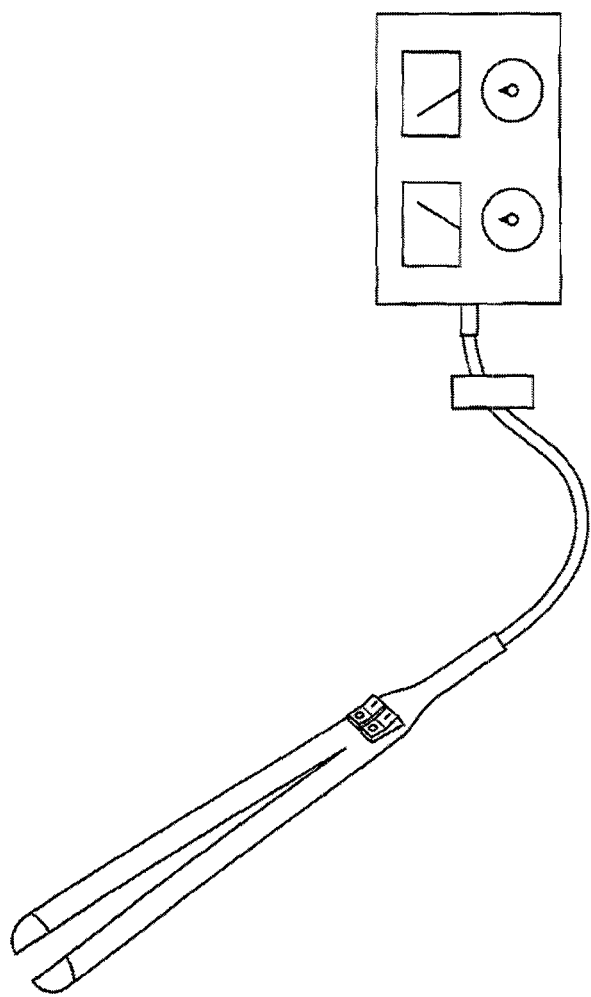
FIG. 38 shows a multi-mode surgical tool with bipolar and thermal modalities.
Figure 39:
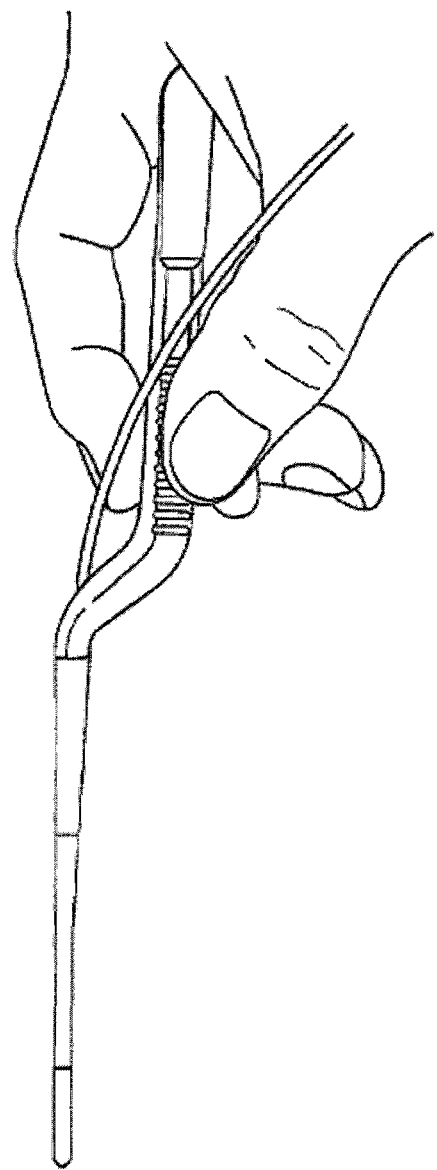
FIG. 39 shows a side view of multi-mode forceps.
Figure 40A:
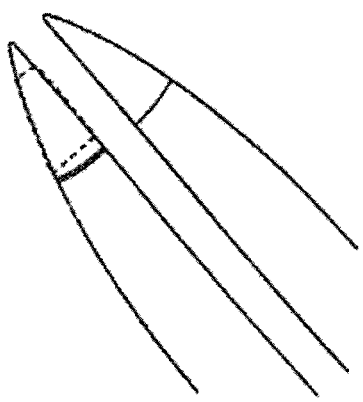
FIG. 40A shows a close-up of an alternate embodiment of forceps tips.
Figure 40B:
FIG. 40B shows a diagram of a coated forceps tip.
Figure 41A:
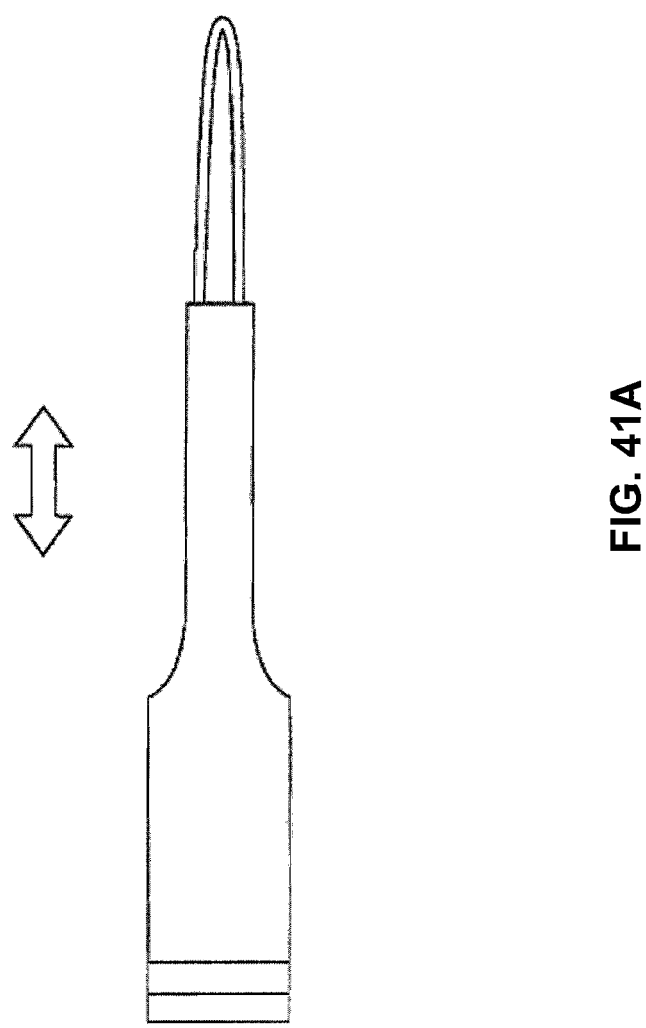
FIG. 41A shows a multi-mode surgical tool with thermal and ultrasonic modalities.
Figure 41B:
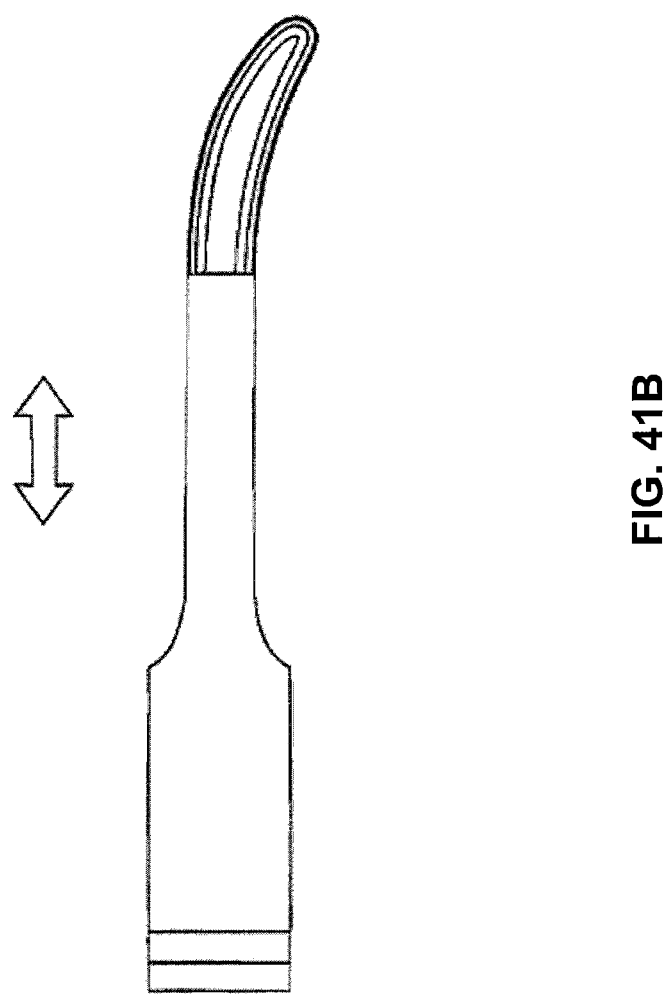
FIG. 41B shows a multi-mode surgical tool with thermal and ultrasonic modalities with a hook primary geometry.
Figure 41C:
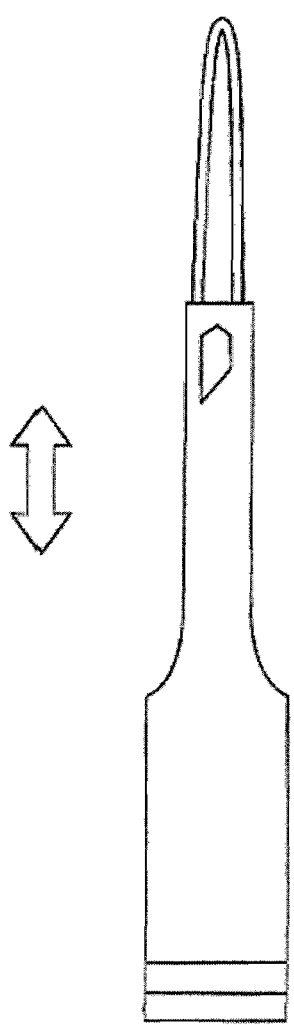
FIG. 41C shows a multi-mode surgical tool with thermal and ultrasonic modalities with a sensor.
Figure 41D:
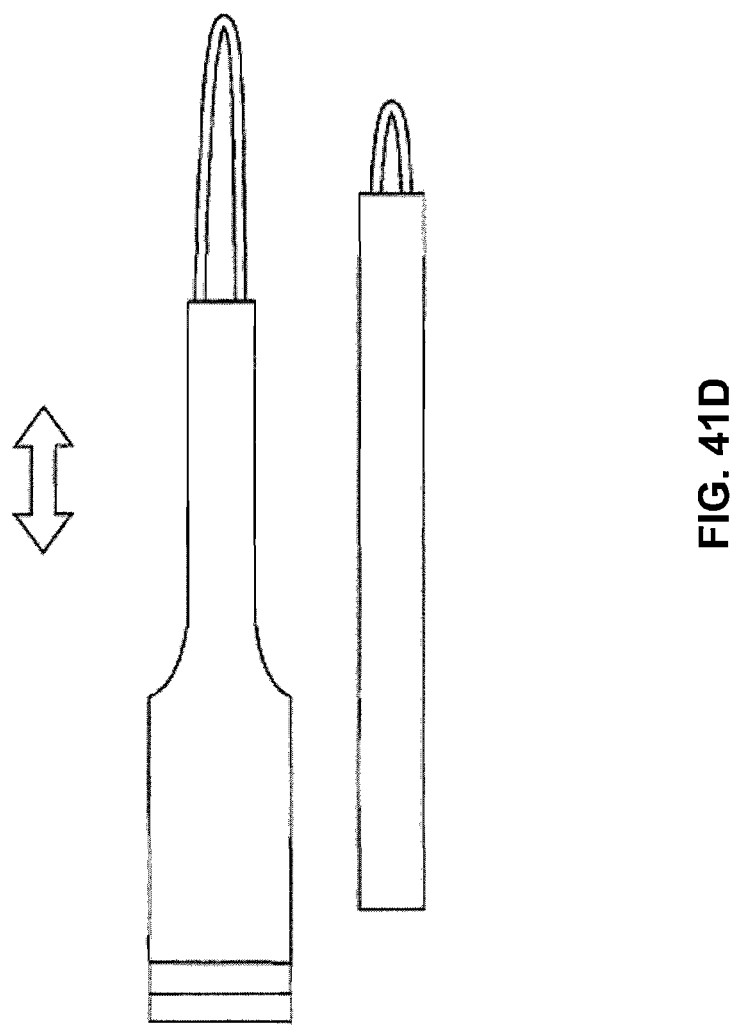
FIG. 41D shows a multi-mode surgical tool with thermal and ultrasonic modalities with a second tip.
Figure 42:
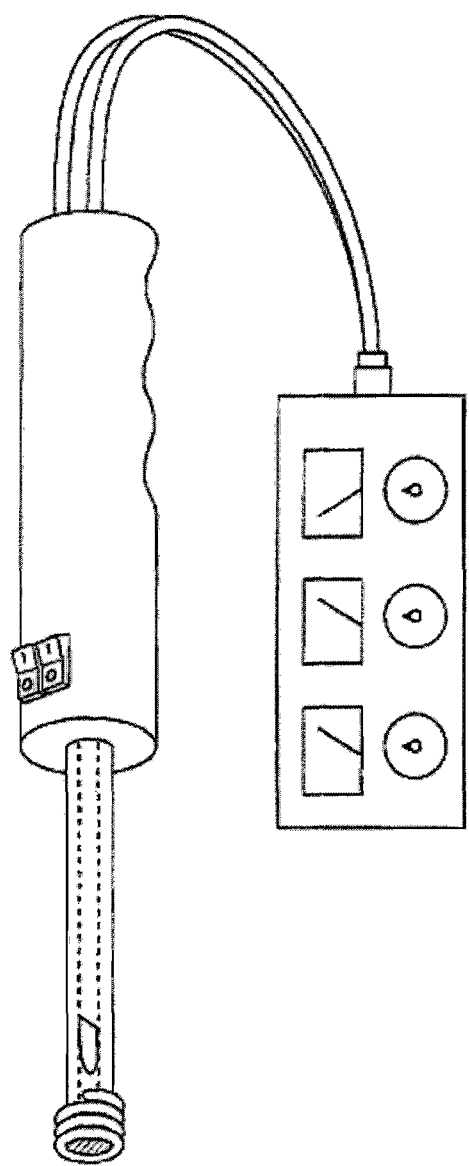
FIG. 42 shows a multi-mode surgical tool with thermal and ultrasonic modalities with aspiration/irrigation and sensor.

Turning now to FIGS. 11A to 13B, a surgical handpiece is shown with a power source, control and handpiece. The surgical element may be a ferromagnetic covered conductor. FIG. 13B shows an autotransformer, which may be another way of matching the load of the thermal element of a surgical tool to a power source.

Turning now to FIGS. 14 to 33, various tip geometries are shown. Each tip configuration may require different base impedance matching circuit component values as well as individual adjustments due to manufacturing tolerances. Tip configurations such as geometry, thicknesses of layers, composition, and length, may all require different matching circuit component values.

Turning now to FIGS. 34 to 42, various surgical tools are shown. The impedance matching circuits may be used with different surgical tools and/or modalities such as catheters (FIG. 34), thermal surgical tools (FIG. 35), mono-polar electrosurgical tools (FIG. 36), bipolar electrosurgical tools (FIG. 38), ultra-sonic surgical tools (FIG. 41A), and multi-mode surgical tools that may combine multiple surgical modalities into one instrument, such as a thermal and bipolar surgical modality.

Figure 43:
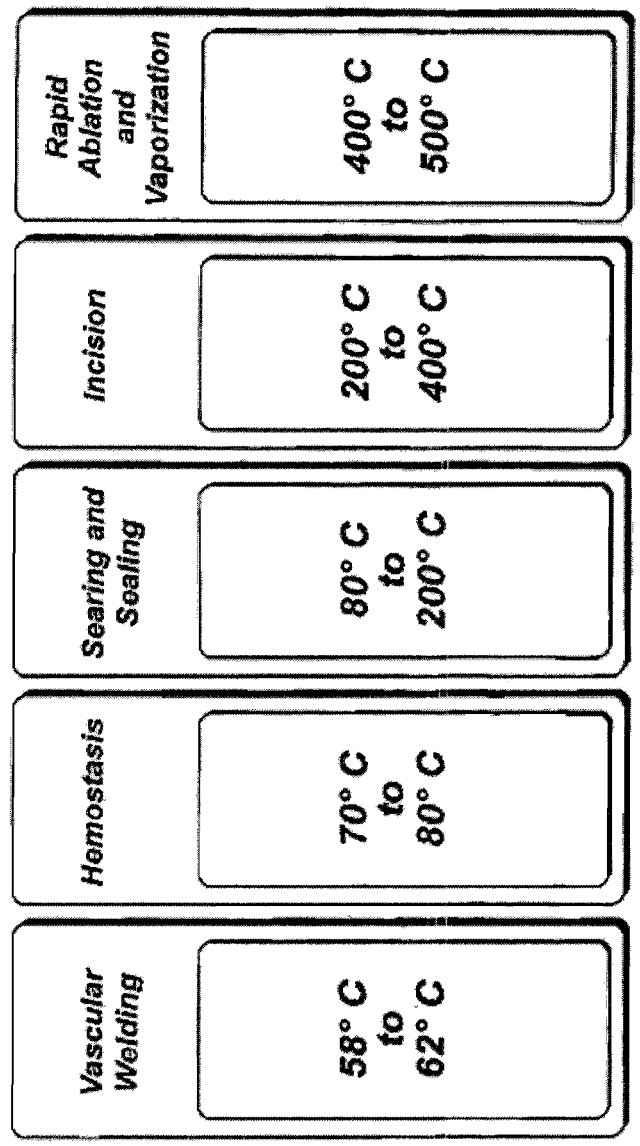
FIG. 43 shows a thermal spectrum as related to tissue effects.

Turning now to FIG. 43, a thermal spectrum as related to tissue effects is shown. With efficient power transfer, such as may be achieved with a correctly adjusted matching circuit, a smaller power source may be used to achieve desired tissue effects than would be required with an inefficient power transfer.

There is thus disclosed an improved impedance matching circuit. It will be appreciated that numerous changes may be made to the present invention without departing from the scope of the claims.

What is claimed is:

1. A thermal surgical instrument comprising:
a thermal element configured to generate thermal energy in response to an electrical signal, the thermal element comprising a ferromagnetic material disposed on an electrical conductor; and
a matching circuit electrically connected to the thermal element;
wherein the matching circuit, in combination with the thermal element, has an input impedance.

2. The thermal surgical instrument of claim 1, wherein the thermal surgical instrument is connectable to a power source, and wherein the input impedance matches the output impedance of the power source.

3. The thermal surgical instrument of claim 1, wherein the thermal surgical instrument is connectable to a power source via a transmission line, and wherein the input impedance matches the impedance of the transmission line.

4. The thermal surgical instrument of claim 1, further comprising a sensor to monitor an indicator of efficiency of power transfer to the thermal surgical instrument.

5. The thermal surgical instrument of claim 1, wherein the input impedance is adjustable.

6. The thermal surgical instrument of claim 5, wherein the input impedance is electronically adjustable.

7. The thermal surgical instrument of claim 1, wherein the matching circuit comprises at least one component selected from the group of a capacitor, inductor, variable capacitor, variable inductor, transformer, coaxial cable, and varactor.

8. The thermal surgical instrument of claim 1, further comprising a data storage unit to store a setting of the thermal surgical element.

9. The thermal surgical instrument of claim 8, wherein the data storage unit is an EEPROM.

10. A thermal surgical instrument comprising:
a thermal element configured to generate thermal energy in response to an electrical signal; and
a matching circuit electrically connected to the thermal element;
wherein the matching circuit, in combination with the thermal element, has an input impedance; and
wherein the matching circuit further comprises a conductive layer disposed on a substrate, wherein at least a portion of the conductive layer is removable.

11. A method of matching an input impedance of a load of a thermal surgical instrument with an output impedance of a power source comprising the steps of:
selecting a thermal surgical tool having a thermal element and a circuit board;
disposing a component on the circuit board to form a matching circuit;
wherein the thermal element and the matching circuit comprise a load having an adjustable input impedance.

12. The method according to claim 11, further comprising measuring an indicator of the load and adjusting the component so that the adjustable input impedance is substantially equal to an output impedance of a transmission line connecting a power source to the thermal surgical instrument.

13. The method according to claim 12, wherein the component comprises a conductive layer, and wherein the method further comprises removing at least a portion of the conductive layer to adjust the input impedance.

14. The method according to claim 12, wherein components are adjusted electronically.

15. The method according to claim 11, further comprising disposing a second component on the board to form the matching circuit.

16. The method according to claim 11, wherein the indicator measured is the standing wave ratio on the transmission line caused by impedance mismatch interaction between the load and source, and wherein the component is adjusted such that the standard wave ratio is substantially 1:1.

17. The method according to claim 11, wherein the component is a varactor, and wherein the method further comprises controlling a voltage applied to the varactor to adjust the input impedance.

18. A method of manufacturing a thermal surgical instrument comprising the steps of:
selecting a surgical instrument comprising a thermal element;
disposing a matching circuit in electrical communication with the thermal element such that the matching circuit, in combination with the thermal element, has an input impedance and wherein the matching circuit comprises a conductive layer; and
adjusting the input impedance by removing at least a portion of the conductive layer so that it matches an output impedance of a power source.

19. The method according to claim 18, further comprising disposing a data storage unit on the thermal surgical instrument, wherein the data storage unit stores settings of the thermal surgical instrument.

20. The method according to claim 18, further comprising disposing a sensor on the thermal surgical element for monitoring an indicator of the thermal element.

21. A thermal surgical tool comprising:
a thermal element;
a circuit board having a component disposed thereon to form a matching circuit; and
wherein the thermal element and the matching circuit comprise a load having an adjustable input impedance.

* * * * *